United States Patent [19]
Rooney et al.

[11] Patent Number: 5,962,318
[45] Date of Patent: *Oct. 5, 1999

[54] CYTOTOXIC T LYMPHOCYTE-MEDIATED IMMUNOTHERAPY

[75] Inventors: Cliona Rooney; Marie Roskrow, both of Memphis; Geoffrey Kitchingman, Millington; Colton Smith, Memphis, all of Tenn.

[73] Assignee: St. Jude Children's Research Hospital, Memphis, Tenn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/746,726

[22] Filed: Nov. 15, 1996

[51] Int. Cl.$^6$ .............................. A01N 63/00; C12N 5/00
[52] U.S. Cl. ...................... 435/325; 435/373; 435/377; 424/93.1
[58] Field of Search ................... 435/325, 172.3, 435/347, 373, 375, 377; 424/93.1

[56] References Cited

U.S. PATENT DOCUMENTS

| | | | |
|---|---|---|---|
| 5,405,940 | 4/1995 | Boon et al. | 530/328 |
| 5,474,935 | 12/1995 | Chatterjee et al. | 435/320.1 |

FOREIGN PATENT DOCUMENTS

WO 98/01538   1/1998   WIPO .

OTHER PUBLICATIONS

I Tarpey et al (1994) Immunology 81: 222–227.
SF Macatonia (1989) J Exp Med 169: 1255–1264.
A Mehta–Damani et al (1994) J Immunology 153: 996–1003.
ABH Bakker et al (1995) Cancer Research 55: 5330–5334.
A Bender et al (1995) J Exp Med 182: 1663–1671.
A Bender et al (1996) J Immunological Methods 196: 121–135.
D Torpey et al (1993) Clinical Immunology and Immunopathology 68: 263–272.
J Lieberman et al (1995) AIDS Research and Human Retroviruses 11: 257–271.
H Koeppen et al (1993) Eur J Immunology 23: 2770–2776.
PG Coulie et al (1993) J immunotherapy 14: 104–109.
T Matsumura et al. (1993) Cancer Research 53: 4315–4321.
Chuck and Palsson [*Human Gene Therapy* 7:743–750 (1996).
Chuck and Palsson, *Biotech. Bioeng.* 51:260–270 (1996).
Hanenberg et al., *Nature Medicine* 2:876 (1996).
Heslop et al., *Nature Med.* 2:551 (1996).
Bender et al., *J. Exp. Med.* 182:1663–1671 (1995).
Flomenberg et al., *J. Infect. Dis.* 171:1090–6 (1995).
Hill and Ploegh, *Proc. Natl. Acad. Sci. USA* 92:341–343 (1995).
Huang et al., *J. VIrol.* 69:2257–63 (1995).
Rooney et al., *Lancet* 345:9–13 (1995).
Smith et al., *J. Hematother.* 4:73–79 (1995).
Souberielle and Russell, *J. Infect. Dis.* 172:1421–1422 (1995).
Stevenson et al., *J. Virol.* 69:2850–7 (1995).
Walter et al., *New Engl. J. Med.*, 333:1038–1044 (1995).
Yang et al., *Proc. Natl. Acad. Sci. USA*, 92:7257–7261 (1995).
Beier et al., J. Immunol. 304:3862–3871 (1994).
Flomenberg et al., *J. Infect. Dis.*, 169:775–781 (1994).
Hromas et al., *Blood*, 84:1689–1690 (1994).
Mathias et al., *J. Virol.* 68:6811–14 (1994).
Romani et al., *J. Exp. Med.* 180:83–93 (1994).
Yang et al., *Nature Genet.*, 7:362–369 (1994).
Berzofsky and Berkower, *Fundamental Immunology, Third Edition*, Paul (ed.), Raven Press, Ltd.: New York, pp. 258–259 (1993).
Wickham et al, *Cell* 73:309–319 (1993).
Riddell et al. [*Science* 257:238–40 (1992).
Tigges et al., *J. Virol.* 66:1622–1634 (1992).
Riddell et al. *J. Immunol.* 146:2795–2804 (1991).
Wold and Gooding, *Virology*, 184:1–8 (1991).
Defer et al., *J. Virol.* 64:3661–73 (1990).
Gooding and Wold, *Crit. Rev. Immunol.*, 10:53–71 (1990).
Rooney et al., *Lancet*, 345:9–12 (1990).
Romani et al., *J. Exp. Med.* 169:1169–1174 (1989).

*Primary Examiner*—Bruce R. Campell
*Attorney, Agent, or Firm*—Kluber & Jackson

[57] ABSTRACT

The present invention is directed to methods for stimulating primary and secondary effector cell responses for cellular immunotherapy. Cellular immunotherapy can successfully prevent or treat various viral infections and tumors, such as posttransplant EBV lymphoma. The present invention offers a general method for effecting cellular immunotherapy by providing for presentation, by the most effective antigen presenting cells, viral particles or specific antigens, without the need to develop an active viral infection in the antigen presenting cells. Furthermore, the present invention provides for generating effector cells against more than one opportunistic pathogen, e.g., Epstein-Barr virus and adenovirus. The effector cells generated according to the invention, which include CD4 and CD8 cells, are extremely long lived in vivo after adoptive transfer. In specific embodiments, dendritic cells present whole adenovirus particles via class I MHC molecules, transduced dendritic cells present a weak EBV antigen to effector cells, and EBV-transformed lymphoblastoid cells present whole adenoviral particles to effector cells, generating a population of effector cells active against EBV and adenovirus. Moreover, the adenovirus-specific effector cells of the present invention, generated against one adenovirus subgroup, recognize different adenovirus subgroups.

33 Claims, 15 Drawing Sheets

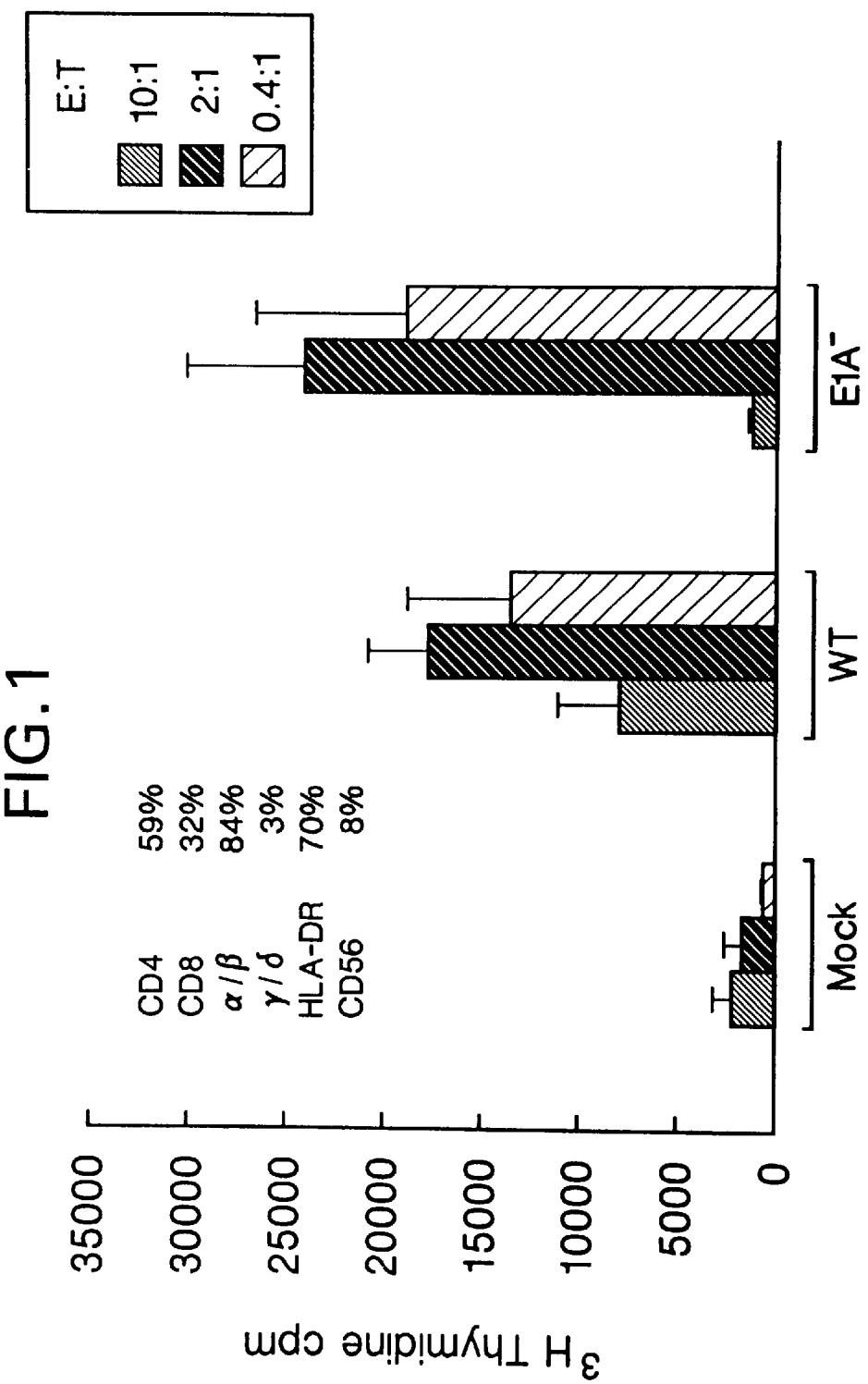

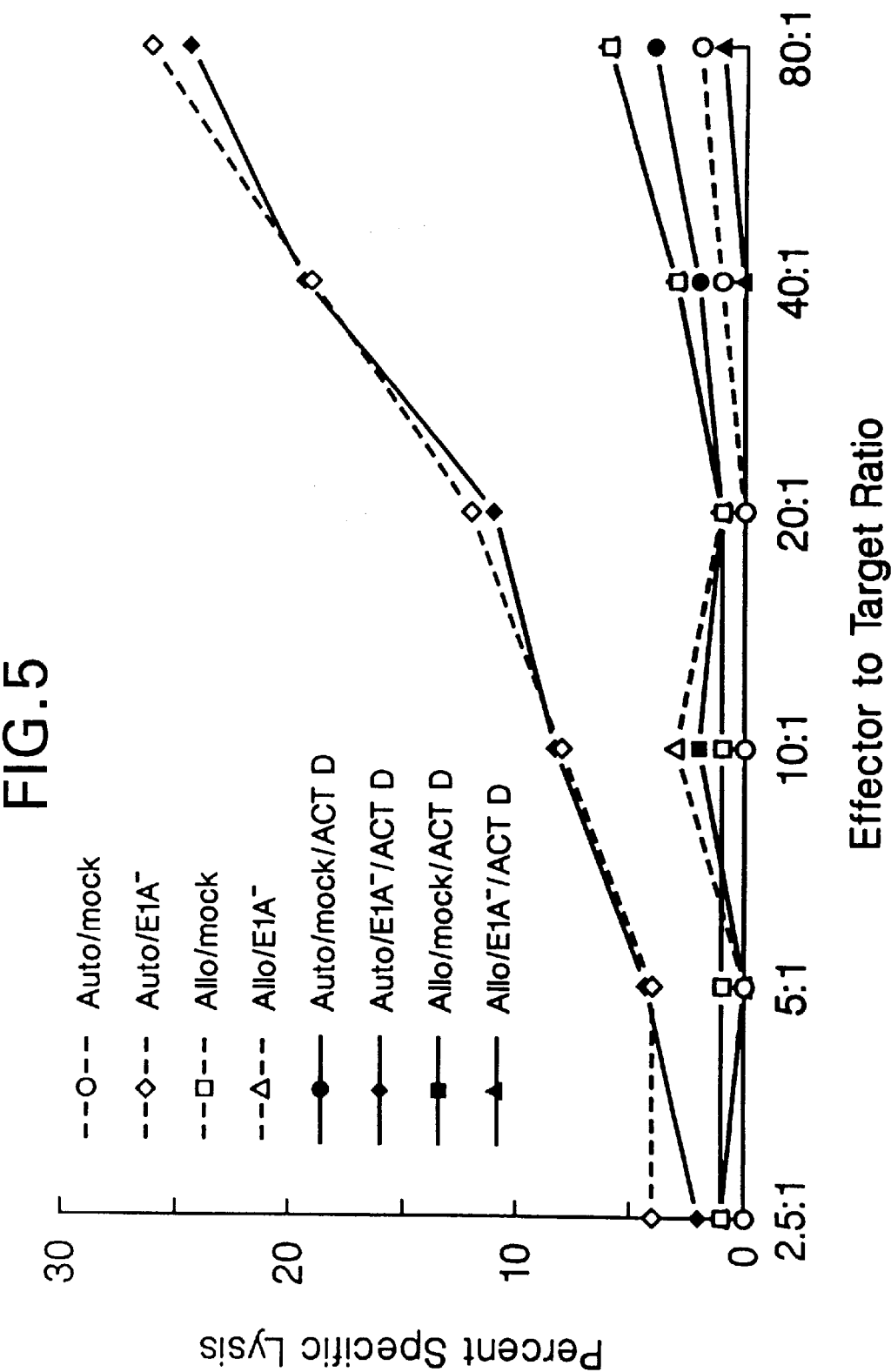

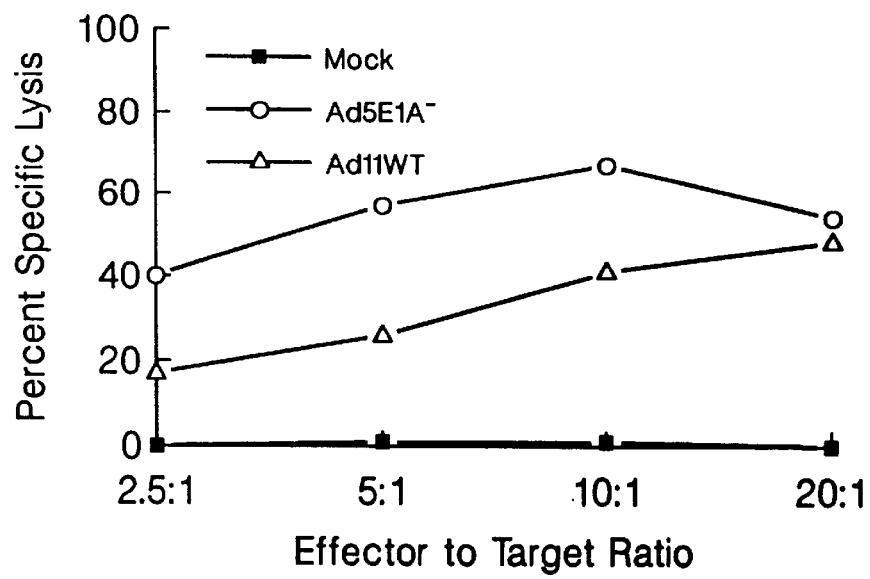
FIG.6A Autologous fibroblasts
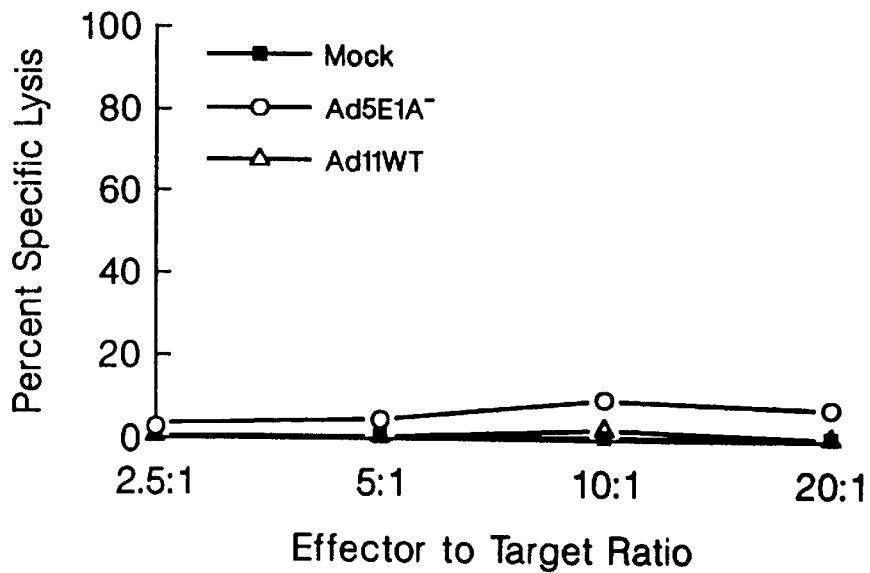
FIG.6B Allogeneic fibroblasts

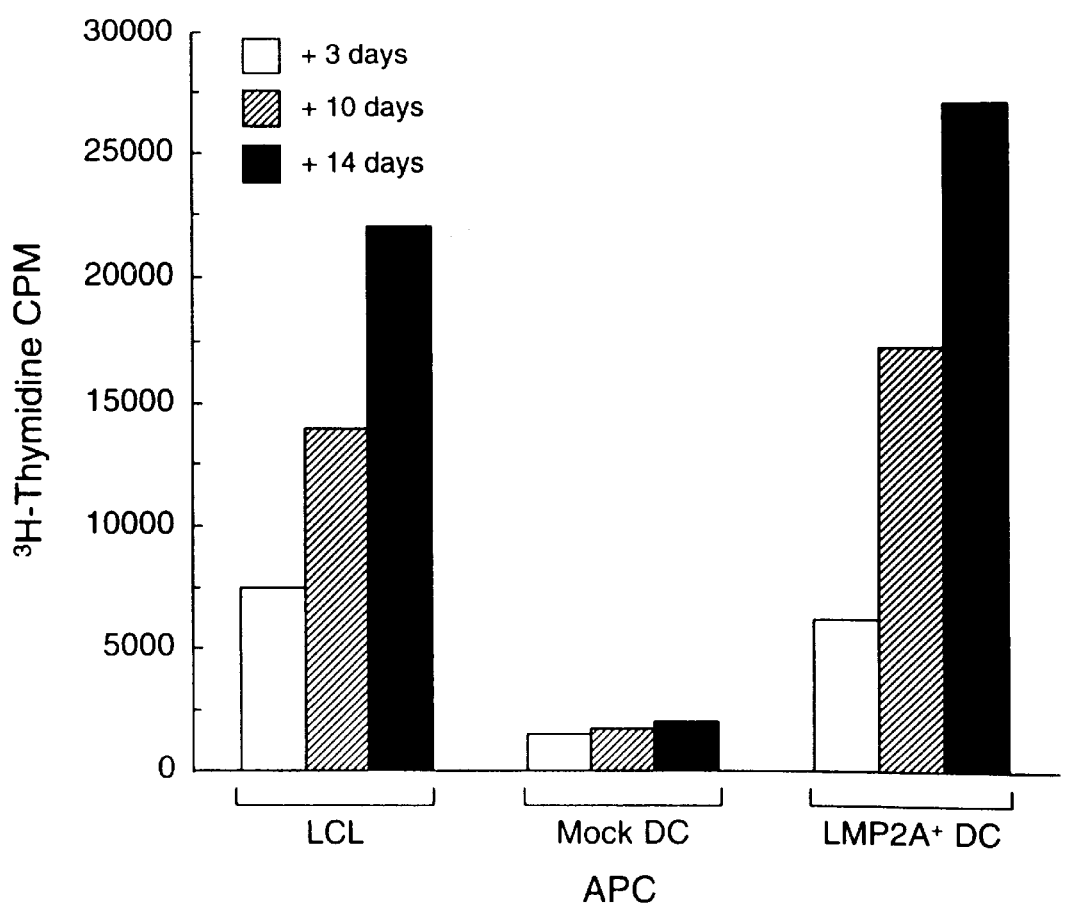

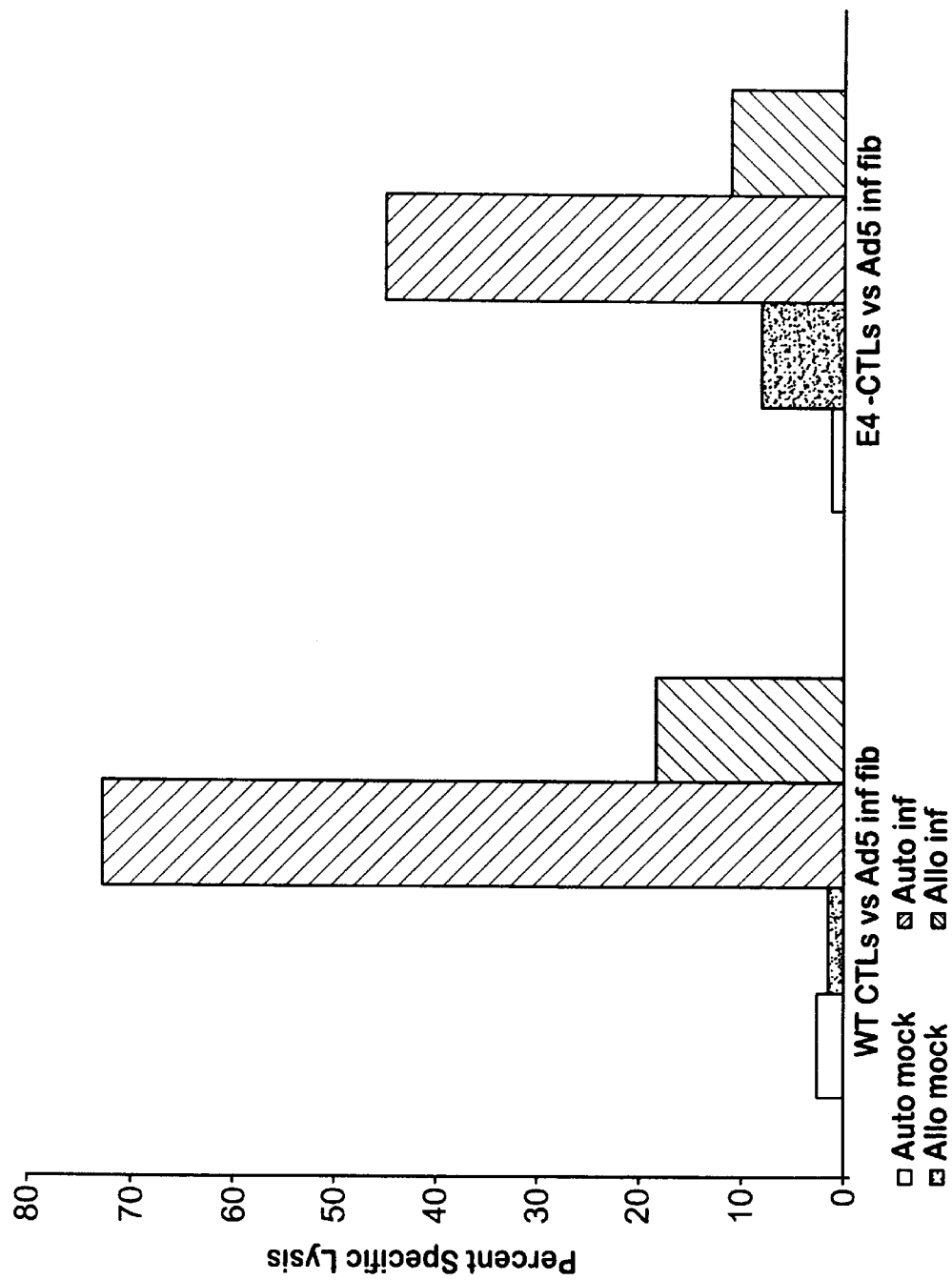

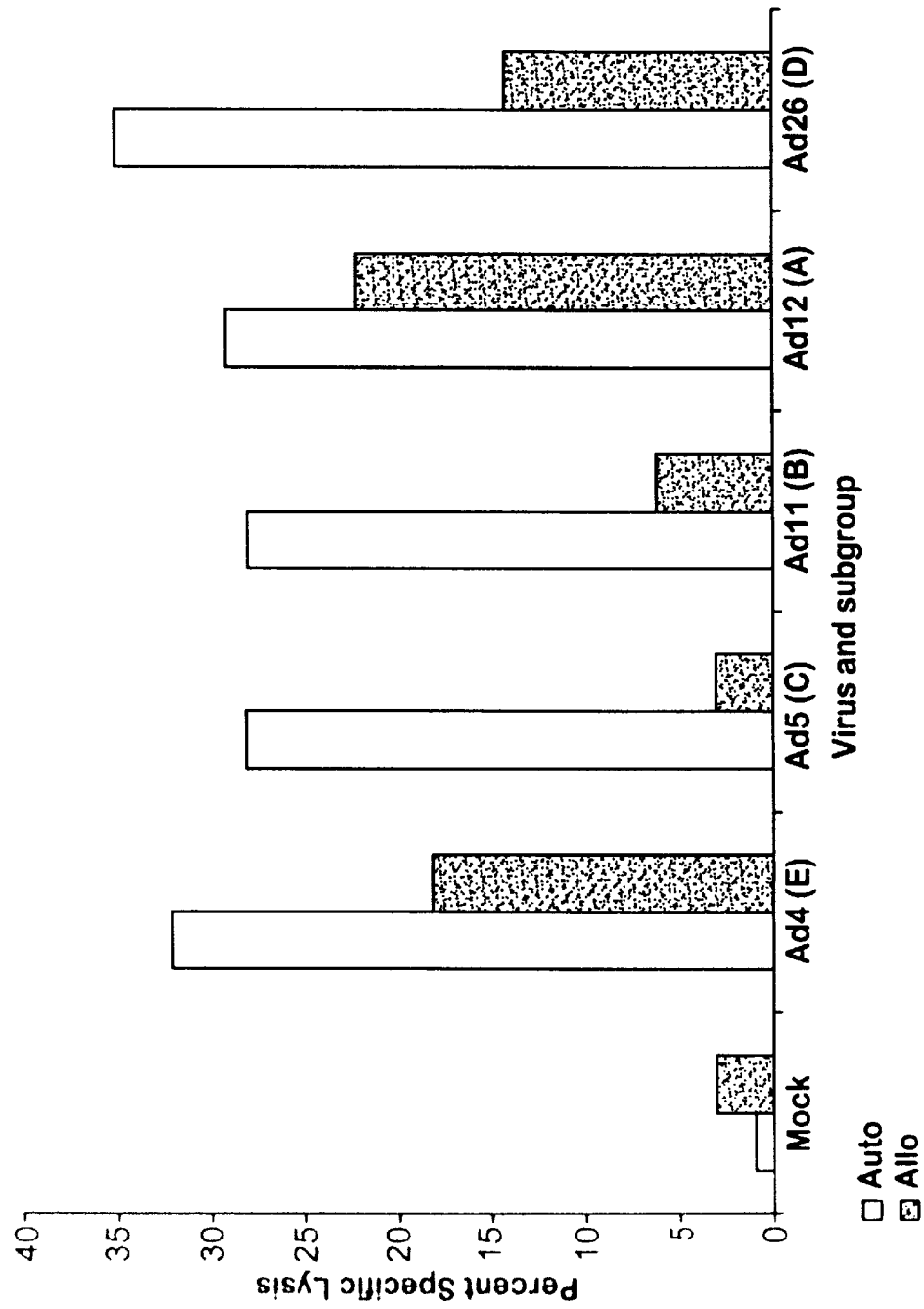

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "PCR primer"

(iii) HYPOTHETICAL: NO (xi) SEQUENCE DESCRIPTION: SEQ ID NO:1:

CATGTTAGGC AAATTGCAAA                                                      20

(2) INFORMATION FOR SEQ ID NO:2:

(i) SEQUENCE CHARACTERISTICS:
      (A) LENGTH: 20 base pairs

-continued

```
    (B) TYPE: nucleic acid
    (C) STRANDEDNESS: single
    (D) TOPOLOGY: linear (ii) MOLECULE TYPE: other nucleic acid
    (A) DESCRIPTION: /desc = "PCR primer"

(iii) HYPOTHETICAL: NO (xi) SEQUENCE DESCRIPTION: SEQ ID NO:2:

ATGACTCATC TCAACACATA                                           20
```

CYTOTOXIC T LYMPHOCYTE-MEDIATED IMMUNOTHERAPY

The research leading to the present invention was supported, at least in part, by a grant from The National Cancer Institute, Grant No. CA 61384, and the Cancer Center Support CORT Grant CA 21765. Accordingly, the Government may have certain rights in the invention.

FIELD OF THE INVENTION

The present invention is directed to methods for stimulating primary and secondary effector cell responses for cellular immunotherapy. Cellular immunotherapy can successfully prevent or treat various viral infections and tumors, such as posttransplant EBV lymphoma. The present invention relates to methods for effecting cellular immunotherapy by providing for presentation of viral particles or specific antigens to effector cells, by the most effective antigen presenting cells without the need to develop an active viral infection in the antigen presenting cells. Furthermore, the present invention relates to generating effector cells specific for more than one opportunistic pathogen, e.g., Epstein-Barr virus and adenovirus.

BACKGROUND OF THE INVENTION

Immunocompromised patients lack a fully active and effective immune system, and are vulnerable to infection by a host of opportunistic organisms that are effectively controlled in a healthy individual. Cancer patients and transplant recipients are especially vulnerable to these infections since their therapeutic regimen often includes radiation and chemotherapeutic agents, which compromise the immune system. Immunodeficient patients, such as AIDS and SCID patients, are also at high risk from these opportunistic pathogens. In particular, patients undergoing bone marrow transplantation (BMT) are severely immunocompromised until their immune systems reconstitute. During the period prior to reconstitution, these patients are susceptible to serious, and sometimes fatal, virus infections caused by normally benign viruses such as adenovirus, cytomegalovirus (CMV), and Epstein-Barr virus (EBV).

In a normal individual, recognition and destruction of virally infected cells is performed principally by $CD8^+$ cytotoxic T lymphocytes (CTLs). The mounting of a CTL immune response requires that the viral proteins undergo intracellular processing to peptide fragments. Selected peptides of defined length are subsequently presented at the cell surface in conjunction with MHC class I molecules. This complex provides the first stimulatory signal recognized by the specific cytotoxic T lymphocyte.

Processing of antigens for presentation by class I MHC involves a complex cellular process (Berzofsky and Berkower, *Fundamental Immunology*, Third Edition, Paul (ed.), Raven Press, Ltd.: New York, pp. 258–259 (1993)]. Unlike processing of exogenous antigen via endosomal pathways for presentation by class II MHC, antigen presented by class I MHC generally must be synthesized endogenously and processed by a nonendosomal pathway into peptides. However, exogenous antigens can enter the cytoplasm for processing by the nonendosomal pathway and presentation by class I MHC.

Although all viral proteins are potential sources of immunogenic peptides, in many situations the actual CTL response is induced by only a small number of immunodominant peptide epitopes derived from a select group of viral proteins. The precise nature of such immunodominance is not clearly understood, but many factors, e.g., the host's T cell receptor repertoire, the ability of an individual protein to access the MHC pathway and the peptide-MHC interaction, have been shown to be important.

EBV Lymphoproliferative Diseases Following Bone Marrow Transplantation

EBV Lymphoproliferative disease occurs in 3–30% of BMT recipients who receive marrow from unrelated donors, and manifests itself as an aggressive B-cell lymphoma which is almost always fatal. The BMT patients are unable to mount a strong immune response sufficient to eradicate the malignancy, but cellular immunity can be strengthened by ex-vivo expansion of a CTL population from the normal BM donor which is then infused into the patient. Replenishment of CTLs to the BMT patient must, however, be accomplished without including certain donor T lymphocytes which would attack healthy cells of the patient, thereby causing an often fatal graft-versus-host disease (GVHD).

Physicians have been treating these BMT patients using infusions of donor-derived CTLs, which specifically recognize and destroy EBV-infected tumor cells. This specific population of CTLs is grown and expanded in culture, and then reinfused into the patient for both prophylactic and therapeutic use. The trial has demonstrated a successful outcome. Of the 25 patients treated prophylactically, none have developed EBV-related diseases nor have any developed GVHD. Four of the 25 patients showed high levels of EBV which would predict onset of the disease, but all of these patients responded to CTL infusion. Without such infusion, 15% of patients develop post-transplant EBV-disease, with 75% fatality using mismatched or unrelated donor marrow. In addition, EBV-specific CTLs were successfully used therapeutically to cure two post-BMT patients who received CTLs after developing life-threatening EBV-lymphomas [Heslop et al., *Nature Med.*, 2:551 1996); Rooney et al., *Lancet* 345:9–13 (1995)].

Hodgkin Disease

Epstein-Barr virus is a gammaherpes virus trophic for pharyngeal epithelial cells and B lymphocytes that displays differential immunogenicity of its viral proteins. This becomes particularly important when one considers the association of EBV with malignant diseases, e.g., Hodgkin's disease, nasopharyngeal carcinoma, and EBV-lymphoproliferative disease. If such diseases are to be treated by adoptive transfer of cytotoxic T-lymphocytes, then one would seek to expand CTLs specific for the particular viral antigens expressed on the tumor cell surface.

Current combined modality therapy for Hodgkin Disease (HD), a pediatric lymphoma, results in a 60–95% cure rate, but relapsed HD carries a poor prognosis and the therapy is very toxic, resulting in second malignancies at a young age in 20% of survivors. At least 50% of HD patients exhibit EB virus in their malignant cells.

In the case of HD, the malignant cells only express three EBV derived antigens, namely EBNA-1, LMP-1 and LMP-2a. Although LMP-1 and LMP-2a have been shown to elicit a cytotoxic T lymphocyte response in vivo, both of them are only weakly immunogenic in comparison with other EBV derived antigens, such as EBNA3c. EBNA-1, although able to elicit an antibody response, has not been demonstrated to stimulate a specific CTL response in vivo. This "non-expression" of the more highly immunogenic proteins is probably one mechanism whereby Hodgkin tumor cells escape immune surveillance.

In such a situation, one may wish to isolate and expand the CTL clone(s) that specifically recognizes the subdominant antigen of choice, e.g., LMP-2a, or one may wish to develop methods for culturing CTLs in vitro that only recognize LMP-2a, i.e., they are monospecific. In order to maximize the T cell response to a weak immunogen, the target antigen would need to be expressed on the surface of a powerful antigen presenting cell. Thus, there is a need in the art to develop a system that provides for high level presentation of the weak antigen on an effective antigen presenting cell. There is a further need to generate antigen specific CTLs to induce both primary and memory T cell responses to a subdominant antigen. There is still a further specific need to develop a transduction system that provides for high level expression of a foreign gene in antigen presenting cells, and application of such a system to generate CTLs for the treatment of malignancies expressing specific viral or tumor antigens.

Adenovirus Disease

Adenovirus infections may be lethal to immunocompromised patients who have received chemotherapy, bone marrow transplants, or other organ transplants. Pediatric BMT patients are particularly susceptible, with 10–30% developing adenovirus infection. A portion of these patients develop adenovirus disease, and one half of those patients die.

There are approximately 50 serotypes of human adenovirus, which are divided into six families based on immunological, molecular, and functional criteria [Wadell et al, *Ann. N.Y. Acad. Sci.* 354:16–42 (1980)]. Physically, adenovirus is a medium-sized icosahedral virus containing a double-stranded, linear DNA genome which, for adenovirus type 5, is 35,935 base pairs (Chroboczek et al., *Virology* 186:280–285 (1992)]). To initiate infection, adenovirus binds to a receptor whose identity is currently unknown [Defer et al., *J. Virol.* 64:3661–73 (1990): Stevenson et al., *J. Virol.* 69:2850–7 (1995)], and then is internalized following binding to a second protein, which has recently been identified as the vitronectin receptor [Huang et al., *J. Virol.* 69:2257–63 (1995); Mathias et al., *J. Virol.* 68:6811–14 (1994); Wickham et al, *Cell* 73:309–319 (1993)]. The virus is internalized in endosomes, and the viral core is released and migrates to the nucleus, where viral RNA transcription is initiated.

The majority of people (greater than 85%) have circulating antibodies against several of the common adenovirus serotypes by the time they reach adulthood [Schmitz et al., *Am. J. Epidemiol.* 117:455–466 (1983)]. Infected individuals develop immunity to adenovirus and retain a life-long immunity to the virus [Evans, *Am. J. Hyg.* 67:256–263 (1958); Schmitz et al., supra], although the virus remains in the body in a latent form [Evans, supra; Neumann et al., *Virus Res.* 7:93–97 (1987)]. Adenovirus infections are rarely severe in healthy children or adults, but can be life-threatening in immunocompromised individuals. For example, a recent review of 201 patients who received T cell-depleted allogeneic bone marrow from HLA-mismatched or HLA-matched unrelated donors, found that 42 (21%) shed adenovirus in urine or stool. The percentage was higher in the pediatric population (31.3% versus 13.6%). Thirteen patients had clinical symptoms of adenovirus infection and 7 died of disseminated disease [Flomenberg et al., *J. Infect. Dis.* 169:775–781 (1994)]. Adenoviruses from 5 of the 6 subgroups were found.

The association between severe adenovirus infection and immunodeficiency suggests that adenovirus is normally controlled by the cellular arm of the immune response. However, little is known about the cellular immune response to adenovirus in humans. A recent study indicated that healthy individuals who were seropositive for adenovirus also had cell-mediated memory responses, as demonstrated by the proliferation of helper T cells in response to purified adenovirus virions in vitro. A second recent study demonstrated that purified viral capsid proteins could stimulate proliferation of peripheral blood mononuclear cells in vitro, but the identity of the responding cells was not determined. Several studies of the role NK cells play in the killing of adenovirus-infected human cells have shown that adenovirus sensitizes rodent but not human cells to NK cell killing [Routes and Cook, *J. Immunol.* 144:2763 (1990); Routes et al., *J. Virol.* 65:1450 (1991); Routes et al., *J. Virol.* 67:3176 (1993); Routes and Cook, *Virology* 210:421–428 (1995)]. These differences were ascribed to downregulation of MHC class I antigens on the cell surface of rodent but not human cells following virus infection. These studies cast doubt on the validity of using human adenovirus infection of mice as a model system. The major CTL response against adenovirus infected rodent cells is directed against early viral proteins, either E1A [Routes et al., (1991), supra; Routes et al. (1993), supra], or E2A [Mullbacher et al., *Immunol. Cell Biol.* 67:31–39 (1989); Rawle et al., *J. Immunol.* 146:3977 (1991)]. This contrasts with the preliminary findings in humans that show that viral capsid antigens are the targets of immune effector cells [Flomenberg et al., *J. Infect. Dis.* 171:1090 (1995); Souberielle and Russell, *J. Infect. Dis.* 172:1421 (1995)]. To characterize the key components in the human immune response to adenovirus infection it will be necessary to establish an in vitro system derived from humans to perform the necessary studies. Thus, there is a need in the art to establish an in vitro system that permits induction and analysis of the human CTL response to adenoviruses.

There are no anti-viral compounds that are effective against adenovirus infections, and it may be desirable to adoptively transfer the cellular immune response to control adenovirus infections in immunocompromised individuals, as has been done for Epstein-Barr virus [Rooney et al., *Lancet* 345:9–12 (1995)]. Thus, there is a need in the art to develop an effective CTL response to adenovirus, for application to adoptive transfer therapy in immunocompromised individuals.

Thus, there remains a major challenge to grow adenovirus-specific CTL simply, efficiently, and economically from all donors regardless of their history of exposure to these viruses. Thus, there is a need in the art for an antigen-presenting system in which adenovirus-specific CTL could simultaneously be selected and expanded in vitro. These CTL could protect against adenovirus infections in vivo in a way that is operationally feasible, efficient and economical.

The citation of any reference herein should not be construed as an admission that such reference is available as "Prior Art" to the instant application.

SUMMARY OF THE INVENTION

The present invention provides for generating highly active, long-resident effector cells for cellular immunotherapy. Cellular immunotherapy, i.e., adoptive transfer of activated effector cells, can prevent or treat opportunistic infections in immunocompromised individuals. In addition, by employing the techniques of the invention, cellular immunotherapy can be used to treat infections or tumors in which the relevant antigen is a weak immunogen, thus eluding immune surveillance and activation.

In one embodiment, the invention provides a method for inducing an ex vivo immune response against a virus. This method comprises pulsing modified antigen presenting cells with viral particles, wherein the antigen presenting cells are modified to process whole viral particles for class I MHC presentation of virus antigens without productive viral infection, and contacting the pulsed antigen presenting cells with MHC-matched immune effector cells for a time sufficient to stimulate viral antigen-reactive immune effector cells under conditions permissive for proliferation of viral antigen-reactive immune effector cells, whereby viral antigen-specific immune effector cells are induced. Preferably, immune effector cells are obtained after a further cycle, i.e., at least two cycles, of stimulation with virion-pulsed antigen presenting cells.

Thus, the present invention advantageously and unexpectedly permits generating immune responses using potent antigen presenting cells without requiring active viral infection of the antigen presenting cells. In specific examples, dendritic cells and lymphoblastoid cell line cells pulsed with adenovirus effectively present adenoviral antigens via the class I MHC molecule, and generate a population of adenoviral-specific effector (CD4 and CD8) T cells. An unexpected benefit of this method was that the effector cells recognized other adenovirus subgroups besides the one used to pulse the antigen presenting cells.

A further particular advantage of this aspect of the invention is that transformed or transduced antigen presenting cells can be pulsed with one or more different viral particles, thus generating a population of multi-specific effector cells. In a specific example, infra, EBV-transformed lymphoblastoid cells were pulsed with adenovirus, generating an effector cell population that killed both EBV-infected and adenovirus-infected target cells.

In another embodiment, the present invention provides a method for inducing an ex vivo immune response against a latent virus antigen or a tumor specific antigen. This method comprises transducing an effective number of antigen presenting cells with a vector that expresses a latent virus antigen or tumor specific antigen under conditions that provide for expression of the antigen; activating the transduced antigen presenting cells; and contacting the antigen presenting cells with MHC-matched immune effector cells for a time sufficient to stimulate antigen-reactive immune effector cells under conditions permissive for proliferation of antigen-reactive immune effector cells, whereby latent virus antigen- or tumor specific antigen-specific immune effector cells are induced. In a preferred embodiment, to ensure potent activation of the effector cells, at least 50% of the antigen presenting cells are transduced and express the latent virus antigen or tumor specific antigen. Preferably, immune effector cells are obtained after a further cycle, i.e., at least two cycles, of stimulation with transduced antigen presenting cells.

Thus, a further significant advantage of the present invention is that it permits generating an efficacious effector cell population against a specific antigen, which may be a weak immunogen relative to other viral antigens. Thus, the invention permits targeting latent viral antigens and tumor specific antigens that might otherwise evade the immune system. Similarly, an effector population generated against whole virus pulsed antigen presenting cells may not have significant specificity for the weak antigen. In a specific example, infra, dendritic cells transduced a vector that expresses the weak EBV antigen LMP2a generate primary and secondary LMP2a-specific effector cells. These effector cells target Hodgkin's disease and nasopharyngeal carcinoma. In another aspect of the invention, the transduced antigen presenting cells may themselves be pulsed with one or more different viral particles, to generate a multi-specific effector cell population.

According to both aspects of the invention, preferred antigen presenting cells are dendritic cells. In specific embodiments, the dendritic cells are selected from the group consisting of Langerhans cells, follicular dendritic cells, bone marrow dendritic cells, and blood dendritic cells. In another preferred aspect of the invention, particularly for developing the multi-antigen specific effector cell populations, the antigen presenting cells are lymphoblastoid cell lines.

Generally, effector cells of the invention comprise cytotoxic T lymphocytes, usually CD8 cells, and helper T lymphocytes, usually CD4 cells. Indeed, a further important advantage of the present invention is that, by providing helper T cells in combination with the CTL effector cells, an extremely long-lived, active effector cell population can be generated for cellular immunotherapy.

Viral particles that can be used to pulse the antigen presenting cells include, though they are by no means limited to, the group consisting of adenovirus, cytomegalovirus, Epstein-Barr virus, herpes virus, parainfluenza virus, human immunodeficiency virus (HIV)-1, HIV-2, influenza virus, and rhinovirus.

The invention provides for generating a secondary immune response, i.e., activation of primed effector cells. Secondary immune responses can be readily achieved with any antigen presenting cell. In another embodiment, the invention provides for generating a primary immune response. The ability to generate a primary immune response is particularly important when the response is generated to a weak latent virus or tumor antigen, such as the EBV antigen LMP2a, in which no primed effector cells may be found in the donor population. Generally, for a primary immune response, the antigen presenting cell is a dendritic cell.

According to the invention, a latent virus antigen transduced into an antigen presenting cell can be selected from the group consisting of Epstein-Barr virus, papillomavirus, hepatitis A virus, hepatitis B virus, hepatitis C virus, papovavirus, HIV-1, HIV-2, human T-lymphotrophic virus (HTLV)-1, and HTLV-2. Alternatively, in another aspect, a tumor specific antigen transduced into an antigen presenting cell is selected from the group consisting of prostate-specific antigen (PSA), human leukemia-associated antigen, carcinoembryonic antigen (CEA), MAGE-1, and MART-1. These represent specific embodiments of the invention, and are by no means limiting of the type of latent viral antigen or tumor specific antigen that can be transduced into an antigen presenting cell.

In addition to the foregoing methods, the present invention advantageously provides ex vivo antigen presenting cells that present virus antigens for class I MHC from processed whole viral particles, wherein the antigen presenting cells are selected from the group consisting of dendritic cells and lymphoblastoid cells. Thus, the most potent antigen presenting cells can be used to generate specific effector cell populations for immunotherapy. As pointed out above, the antigen presenting cells may be pulsed with a virus selected from the group consisting of adenovirus, cytomegalovirus, Epstein-Barr virus, herpes virus, parainfluenza virus, human immunodeficiency virus (HIV)-1, HIV-2, influenza virus, and rhinovirus.

In another embodiment, the invention advantageously provides ex vivo antigen presenting cells transduced with a vector that expresses a latent virus antigen or tumor specific antigen under conditions that provide for expression of the latent virus antigen or tumor specific antigen. Preferably, at least 50% of the antigen presenting cells are transduced and express the latent viral antigen or tumor specific antigen. In specific embodiments, the antigen presenting cells are dendritic cells, e.g., Langerhans cells, follicular dendritic cells, marrow dendritic cells, or blood dendritic cells, or lymphoblastoid cell line cells. The antigen presenting cells may be transduced with a vector that expresses a latent viral antigen of a virus selected from the group consisting of Epstein-Barr virus, papillomavirus, hepatitis A virus, hepatitis B virus, hepatitis C virus, papovavirus, HIV-1, HIV-2, human T-lymphotrophic virus (HTLV)-1, and HTLV-2. Alternatively, the antigen presenting cells may be transduced with a vector that expresses a tumor specific antigen selected from the group consisting of prostate-specific antigen (PSA), human leukemia-associated antigen, carcinoembryonic antigen (CEA), MAGE-1, and MART-1.

In a highly preferred embodiment, the invention provides a population of effector cells consisting of effector cells specific for Epstein-Barr virus and effector cells specific for a pathogenic virus, a latent virus antigen, or a tumor specific antigen. The effector cells may be additionally specific for a pathogenic virus selected from the group consisting of adenovirus, cytomegalovirus, Epstein-Barr virus, herpes virus, parainfluenza virus, human immunodeficiency virus (HIV)-1, HIV-2, influenza virus, and rhinovirus; a latent virus selected from the group consisting of Epstein-Barr virus, papillomavirus, hepatitis A virus, hepatitis B virus, hepatitis C virus, papovavirus, HIV-1, HIV-2, human T-lymphotrophic virus (HTLV)-1, and HTLV-2; or a tumor specific antigen selected from the group consisting of prostate-specific antigen (PSA), human leukemia-associated antigen, carcinoembryonic antigen (CEA), MAGE-1, and MART-1.

Thus, the invention very advantageously provides a population of effector cells specific for more than one opportunistic infection, which are useful for prophylaxis in immunocompromised individuals, such as bone marrow transfer recipients, cancer patients undergoing chemotherapy, and organ transplant recipients receiving treatment for a rejection episode.

Thus, it is an object of the invention to generate effector cells against opportunistic pathogens using the most potent antigen presenting cells.

It is a related object of the invention to provide a long-lived, robust population of effector cells for cellular immunotherapy.

It is a further object of the invention to provide a population of effector cells specific for a weak or minor antigen found in latent viral infection or on tumor antigens.

Still another object of the invention is to provide an effector cell population specific for two or more opportunistic pathogens.

A closely related object of the invention is to provide for prophylactic cellular immunotherapy for multiple opportunistic pathogens.

These and other objects of the invention will be readily appreciated by reference to the accompanying drawings, the detailed description of the invention, and the Examples.

BRIEF DESCRIPTION OF THE DRAWINGS

FIG. 1. Proliferation of mononuclear cells (MNCs) in response to irradiated dendritic cells (Den) pulsed with nothing, wild-type adenovirus type 5 (Ad), or dl312 (E1A−), an Ad5 mutant deleted for the E1A region at effector to target ratios of 10:1 (dense diagonal), 2:1 (bold diagonal), and 0.4:1 (open diagonal). The numbers represent counts per minute of $^3$H-thymidine incorporated into DNA. The effector cell population was characterized as follows: 59% CD4; 32% CD8; 84% α/β; 3% γ/δ; 70% HLA-DR (class II); and 8% CD56.

FIG. 5. Cytotoxicity of CTLs assayed against dl312 (E1A−)-infected fibroblasts in the presence (open symbols) or absence (solid symbols) of actinomycin D. CTLs were generated against Ad5 and assayed against mock-(circles, squares) or dl312-infected (diamonds, triangles) autologous (Auto; circles, diamonds) or allogeneic (Allo; squares, triangles) fibroblasts in the presence or absence of 20 μg/ml of actinomycin D (ACT D).

FIGS. 6A–6B. CTLs raised against Ad5 lyse targets infected with Ad11. CTLs were generated against Ad5 and assayed against fibroblasts infected with either Ad5 (open circles) or Ad11 (open triangles) at the indicated effector to target ratios. Mock infected cells (solid squares) were used as controls. (A) Activity against autologous fibroblasts. (B) Activity against allogeneic fibroblasts.

FIG. 9. Tritiated thymidine incorporation assay illustrating that LMP2A-transduced dendritic cells stimulate the proliferation of peripheral blood mononuclear cells to the same degree as does the LCL at all 3 time points.

FIG. 12. Either wild-type- or mutant-pulsed LCLS can be used to generate adenovirus-specific CTLs. LCLS were incubated with the indicated virus at an moi of 100 for one hour at 37 degrees Celsius, irradiated with 3000 rads and then incubated with autologous peripheral blood lymphocytes at a ratio of 40:1. After 10 days, the lymphocytes were re-stimulated at a ratio of 4:1 with similarly treated LCLS. After an additional 4 days, the CTLs were assayed against the indicated targets.

FIG. 14. CTLs raised against mutant Ad5-pulsed LCLS kill fibroblast infected with viruses of different subgroups. CTLs were prepared as in FIG. 13.

DETAILED DESCRIPTION OF THE INVENTION

Figure 2A:
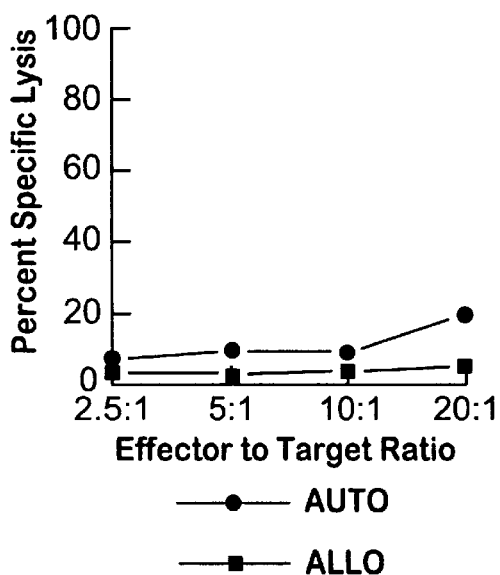
FIGS. 2A–2H. Cytotoxicity and cell-surface phenotype of T cells that grow in response to virus-pulsed dendritic cells. T cell lines were prepared from donors LW (A, C, E, G) and CR (B, D, F, H) and assayed against mock-(A,B), Ad5 (WT)-(C,D), dl312 (E1A−)-(E,F), or dl7001 (E3−)-(G,H) infected fibroblasts. Both autologous (AUTO, solid circle) and HLA-mismatched (ALLO, solid square) fibroblasts were used. CTLs from LW were 52% CD4, 25% CD8, 13% CD56, 87% HLA-DR, 83% α/β, and 2% γ/δ; CTLs from CR were 67% CD4, 27% CD8, 6% CD56, 76% HLA-DR, 91% α/β, and 4% γ/δ.
Figure 2B:
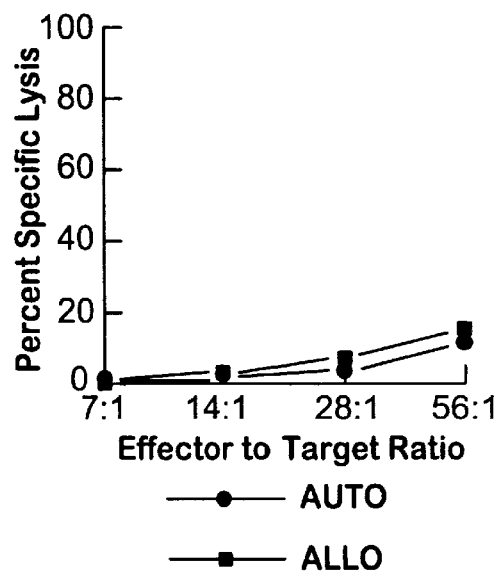
Figure 2C:
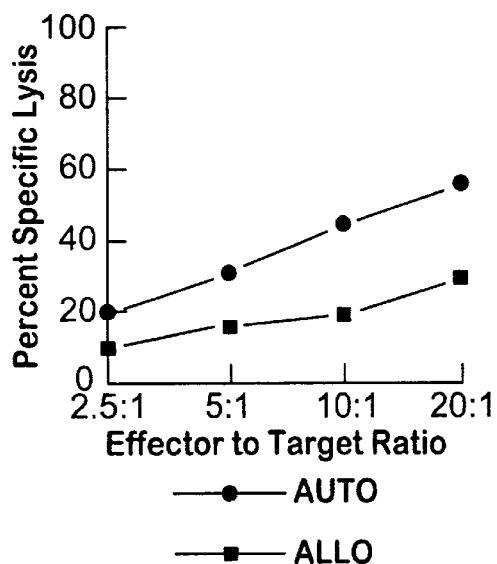
Figure 2D:
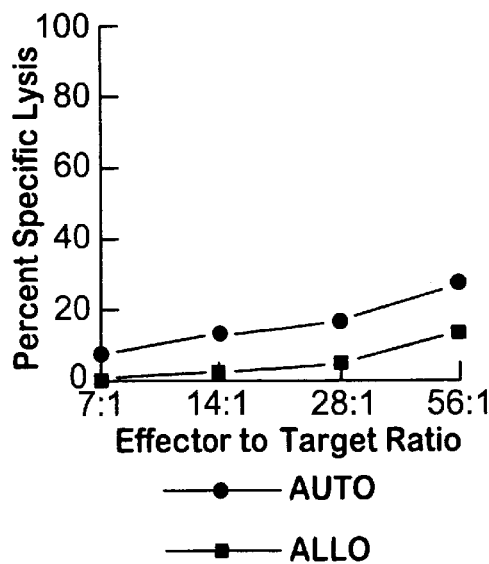
Figure 2E:
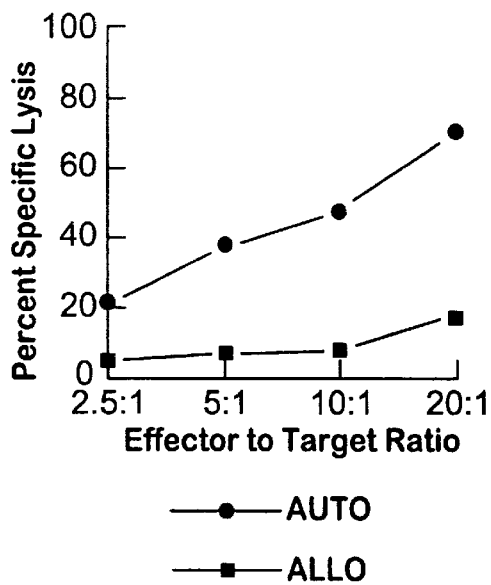
Figure 2F:
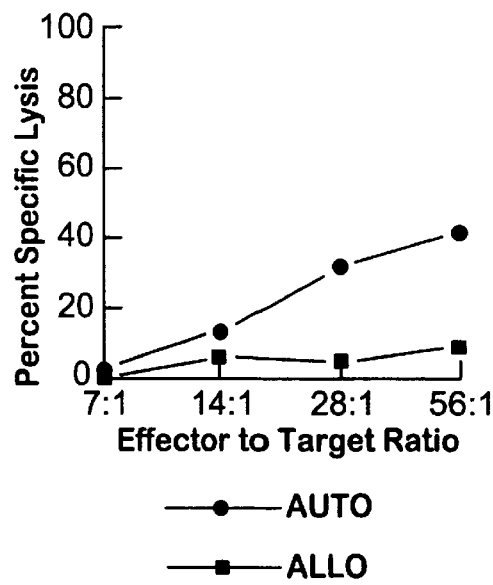
Figure 2G:
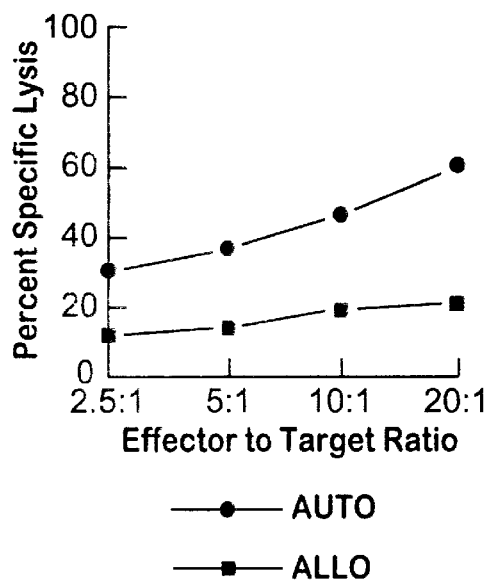
Figure 2H:
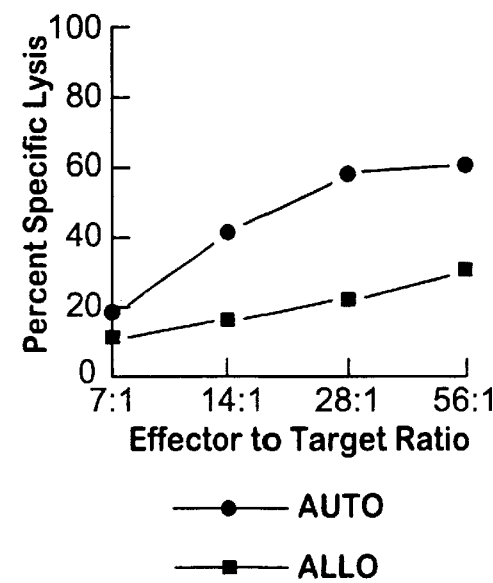

As noted above, the present invention is directed to methods for stimulating primary and secondary effector cell responses for immunotherapy. In principle, immunotherapy can prevent or treat opportunistic pathogenic viral infections or tumors (including viral tumors) in immunodeficient subjects. However, cellular immunotherapy with ultrafractionated donor derived population of T cells can lead to graft-versus host (GVH) disease when a subset of administered T cells cross-react with host antigens. The ability to generate pathogen-specific effector cell populations without engendering GVH disease is critical for successful CTL immunotherapy.

CTL immunotherapy has great promise for treating Epstein-Barr virus (EBV) lymphoproliferative disease and EBV-associated Hodgkin disease following bone marrow transplant (BMT). EBV lymphoproliferative disease occurs in about 3–30% of BMT recipients who receive marrow from unrelated donors. Adenovirus infections are common in patients receiving chemotherapy, organ transplantation rejection therapy, and in 10–30% of BMT patients. CTL immunotherapy has significant potential for treating these infections and for treating other viruses associated with malignancies such as adult nasopharyngeal carcinoma (NPC), and for recipients of organ transplants (who are also at risk for cytomegalovirus, CMV, infection), papillomavirus-induced laryngeal papillomatosis and certain cancers, and in immunocompromised patients, such as acquired immunodeficiency syndrome (AIDS) or severe combined immunodeficiency disease (SCID) patients.

Prior efforts to generate virus-specific CTLs depended on using antigen presenting cells actively infected with virus as stimulators. For example, Riddell et al. [Science 257:238 (1992)] described generating human CMV-specific CTL clones in vitro with CMV-infected fibroblasts as the stimulating cells. Riddel used CD8$^+$clones (no CD4 cells were present), which persist only for 6–12 weeks [as described in Walter et al., NEJM 333:1038 (1995)]. The present invention uses CD8$^+$ and CD4$^+$cells (which maintain survival of CD8$^+$ cells), and thereby permitting CTLs to persist for many months. Rooney et al. [Lancet 345:9–13 (1995); see also Heslop et al., Nature Med. 2:551 (1996)] describe stimulating EBV-specific CTLs with EBV-transformed B cell lymphoblastoid lines. As shown in the Examples, infra, the present invention provides a number of advantages over the prior art by providing for presentation of viral particles or specific antigens to effector cells by the most effective antigen presenting cells, without the need to develop an active viral infection in the antigen presenting cells.

First, as shown in the Examples, infra, class I MHC-restricted antigen presentation can be achieved with whole virions, in the absence of productive viral infection of the antigen presenting cells by the virus. In other words, the invention is based, in part, on the unexpected discovery that whole virus can be processed and presented in the context of class I MHC, without requiring cellular expression of viral antigens and subsequent fragmentation of viral antigens into peptides. In specific examples, two different antigen presenting cell populations were employed to achieve this result: dendritic cells and lymphoblastoid cells. Thus, the invention provides for induction of primary or secondary immune responses against viruses that do not actively infect the antigen presenting cell, thereby eliminating contamination of cell populations with infectious virus.

Second, as shown in the Examples, infra, antigen presenting cells, particularly dendritic cells, can be transduced with nucleic acid encoding viral or tumor antigens to generate potent primary or secondary immune responses against these antigens. More importantly, the transduced antigen presenting cells can generate strong responses to relatively weak immunogenic or non-immunogenic antigens. In a specific example, CTLs are generated against the weak EBV antigen LMP-2a. These CTLs are excellent candidates for immunotherapy for Hodgkin's disease and NPC, in which the tumors only express such weak EBV antigens.

Third, as shown in the Examples, strong immune responses can be developed against more than one viral pathogen. In the specific embodiment, a population of effector cells consisting of cells specific both for EBV antigens and for adenovirus antigens is generated. This is an unexpected but extremely gratifying result since prior to the instant invention, the expectation would have been that the cells specific for one or the other virus would dominate the effector cell population. An effector cell population specific for more than one pathogen is highly advantageous prophylactically, since these cells would survey and control EBV and adenovirus, and potentially other pathogens such as CMV, in immunocompromised subjects.

The present invention relates generally to the field of immunology. Various terms and methods can be found in the leading texts and immunology publications. One important text is William Paul's Fundamental Immunology, Third Edition Raven Press Ltd: New York (1993), which is incorporated herein by reference in its entirety. Other useful texts include Hood et al., Immunology, Second Ed., Benjamin/Cummings: Menlo Park, Calif. (1984), Current Protocols in Immunology, Volumes I–III, Coligan, J. E., ed. (1994), Manual of Clinical Laboratory Immunology, Third Edition, N. R. Rose et al., American Society for Microbiology (1986), each of which is incorporated herein by reference. In addition, various terms used in this specification are more fully described in the following sections of the application, which are provided for convenience and not by way of limitation. Other terms have definitions as set forth:

As used herein, the term "antigen presenting cell" refers to an immune accessory cell that participates in antigeninductive events, and includes mononuclear phagocytes, dendritic cells, and B cells, which express high levels of class I MHC. In a specific embodiment, the B cell antigen presenting cell is a lymphoblastoid cell or lymphoblastoid cell line (LCL), i.e., a B cell transformed by infection with Epstein-Barr virus (EBV). In a another specific embodiment, the antigen presenting cell is a dendritic cell. Autologous antigen presenting cells, i.e., antigen presenting cells obtained from the same donor as the effector cells, are preferred. Alternatively, class I MHC-matched antigen presenting cells from a different donor can be used with autologous T cells.

A "modified antigen presenting cell" refers to an antigen presenting cell treated to process via the class I MHC molecule viral particles that are not actively infectious in the cells via the class I MHC molecule. Generally, antigen presenting cells are treated to induce maturation or activation, e.g., by culturing, preferably in the presence of a specific growth or stimulatory factor or factors. In specific embodiments, infra, dendritic cells are modified by culturing with GM-CSF to process and present whole viral particles. B cells transformed with EBV are considered modified in accordance with the invention.

"Transduced antigen presenting cells" refer to antigen presenting cells that have been effectively transfected or transformed with a vector that expresses an antigen, such as a latent virus antigen or a tumor antigen, such that the antigen is expressed and presented via class I MHC by the antigen presenting cell. Preferably, more than about 30% of the antigen presenting cells are transduced; more preferably, more than about 50% of the antigen presenting cells are transduced; still more preferably, more than about 60% of the antigen presenting cells are transduced. In a specific embodiment, infra, 60% of dendritic cells were successfully transduced. This is especially remarkable because dendritic cells are notoriously refractory to transduction.

The term "effector cell" as used herein refers to the cells of the immune system that mount responses to protect individuals from pathogens, preferably viruses, tumor viruses, and tumors (including viral and non-viral tumors) [see *Fundamental Immunology*, Third Edition, p. 18]. A preferred effector cell of the invention is a population of cytotoxic T cells and T helper cells that host cellular immunity. An advantage of the present invention is that the presence of both cell types enhances cellular immunity, both in terms of vigor and length. Cytotoxic T cells (CTLs) generally are CD8-positive (CD8$^+$, or simply CD8), and class I MHC-restricted, although CD4-positive (CD4$^+$, or simply CD4) cytotoxic T cells and class II MHC-restricted CD8 cells have also been identified (Fitch et al., *Fundamental Immunology*, Third Edition, pp. 748–750). Most such cells express an $\alpha, \beta$-T cell antigen receptor-CD3 complex, which is antigen specific. Some CD8-positive cells may express a $\gamma,\delta$-T cell antigen receptor-CD3 complex, which does not seem to be antigen specific. In addition to the CTL effector cells, virus- or antigen-specific effector cells generated using the methods and unique antigen presenting cells of the invention include CD4-positive (class II MHC restricted) cells, also termed helper T cells. Immunologists have identified two subpopulations of helper T cells ($T_h$ cells), Th1 cells, which appear to help CTL responses, and which are the preferred subpopulation in the specific effector cells generated by the invention, and Th2 cells, which are associated with humoral immune response help. In addition to antigen-specific (CD4, CD8, T cell receptor-positive) effector T cells, the effector cell populations of the invention may include CD56-positive natural killer (NK) cells and lymphokine-activate killer (LAK) cells, and B cells.

The terms B-cell and B-lymphocyte are used interchangeably and synonymously herein. Similarly, the terms T-cell and T-lymphocyte are used interchangeably and synonymously herein.

A molecule is "antigenic" when it is capable of specifically interacting with an antigen recognition molecule of the immune system, such as an immunoglobulin (antibody) or T cell antigen receptor. An "immunogenic" molecule is an antigen capable of eliciting an immune response, e.g., a whole protein or organism. An antigenic polypeptide contains at least about 5, and preferably at least about 10, amino acids. As used herein, the term "antigen" refers to a protein from a pathogen that is targeted by effector cells of the cellular immune system.

The present invention advantageously provides for targeting immunodominant viral antigens, which are likely to be most relevant where active infectious virus and viral particles are present with morbidity, by pulsing antigen presenting cells with the viral particle (i.e., virion). The invention also advantageously provides for targeting specific antigen, which is necessary where an efficacious immune response requires recognition of a specific antigen or antigens, by effectively transducing the antigen presenting cells with a vector for expression of the specific antigen. This may be the case where latent viral infection is associated with morbidity or mortality, such as with tumor viruses, or hepatitis virus infections, and with tumor antigens. In these circumstances, infected or transformed cells may only present a single viral antigen (termed herein a "latent virus antigen") or a tumor specific antigen. Furthermore, in cases where the latent viral antigen or tumor antigen is a weak immunogen, the present invention advantageously provides for generating an immune response against that specific antigen, which permits effective immunotherapy for a pathogen that is effectively invisible to the compromised immune system.

The term "pathogen" is used to refer to pathogenic viruses, latent viruses (especially tumor viruses), and tumors. "Pathogenic viruses" are those viruses in which the active virus particle replication is the cause of morbidity. A "latent virus" is a virus that exhibits pathogenic effects in its latent phase, and includes hepatitis viruses and tumor viruses, such as EBV and HPV. A tumor is a transformed cell, such as a cancer cell, which may express tumor-specific antigens that can serve as targets for stimulating effector cell responses according to the invention.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function, and response of the host. Alternatively, a therapeutically effective amount is sufficient to cause an improvement in a clinically significant condition in the host. In the context of the present invention, a therapeutically effective amount of effector cells is a number that is effective to treat an opportunistic viral infection or tumor in an immunocompromised host. Preferably, the effective amount (or number) of effector cells resolves the underlying infection or cancer.

In a specific embodiment, the term about means within about 20%, preferably within about 10 %, and more preferably within about 5%.

Antigen Presenting Cells

Dendritic Cells

The term "dendritic cell" is used herein to refer to the active antigen presenting cells found in epithelia and thymus-dependent areas of lymphoid tissues [see Unanue, *Fundamental Immunology*, Third Edition, Paul (ed.), Raven Press, Ltd.: New York. pp. 119–121 (1993)]. They are characterized by their peculiar dendritic morphology and multiple thin-membrane projections, and by a high density of class II MHC molecules. Dendritic cells include Langerhans cells of the skin, "veiled cells" of afferent lymphatics, follicular dendritic cells, dendritic cells of the spleen, and interdigitating cells of lymphoid organs. Dendritic cells can be obtained from the skin, spleen, bone marrow, or other lymphoid organs, lymph nodes, or blood. Preferably, dendritic cells are obtained from blood or bone marrow for use as APCs of the invention.

It has been found that explants of mouse [Larsen et al., *J. Exp. Med.* 172:1483–1493 (1990)] or human skin [Richters et al., *J. Invest. Dermatol.* (1994)] placed in organ culture permit selective migration of dendritic cells into the medium surrounding the explant. Alternatively, dendritic cells can be obtained from blood as described in the Examples, infra, from spleen, lymph nodes, or organs (such as the heart, lung, and liver; see Unanue, supra). Dendritic cells are found in the epithelia [Nestle et al., *Cell. Immunol.* 156:220–229 (1994)].

In a specific embodiment, Langerhans dendritic cells can be obtained from skin explants. In a specific embodiment, skin is washed twice with sterile $Ca^{++}$ and $Mg^{++}$-free PBS, incubated in medium with 200 μg/ml Gentamicin (Gibco BRL) for 1 hr at 4° C., washed twice in sterile $Ca^{++}$ and $Mg^{++}$-free PBS, and floated as 3×3 cm explants dermal side down, each in 15 ml of medium in 100 mm dishes (#3003, Falcon, Oxnard, Calif.). After 2–5 days at 37° C., the skin is removed and the debris digested with 400 units/ml Collagenase D (#1088 882, Boehringer Mannheim [BM], Indianapolis, Ind.) for 1 hr at 37° C. This ensures harvesting the cells without marked losses due to trapping within collagenous debris. The cells are pooled, washed in medium, and the numbers of viable cells (>95%) assessed by Trypan blue (Gibco BRL) exclusion. Skin cells can also be prepared from epidermal sheets and dermal explants as described [Lenz et al., *J. Clin. Invest.* 92:2587–2596 (1993); Romani et al., *J. Invest Dermatol.* 30 93:600–609 (1989)]. Dendritic cells may be enriched by floatation on 13.5% metrizamide [Kripke et al., *J. Immunol.* 145:2833–2838 (1990)].

Langerhans cells can be stimulated to express antigen by permitting maturation, e.g., by culturing the cells for 24 to 48 hours. As used herein, the term "dendritic cell maturation" and its variants relates to the phenotypic changes the dendritic cell undergoes, and the role it plays in activating T lymphocytes. Accordingly, the term maturation includes, but is not limited to. upregulation of MHC, and expression of certain accessory and activation molecules, such as CD80/B7-1. CD86/B7-1, CD54/immune cell adhesion molecule-1 (ICAM-1), and CD25/interleukin-2 (IL-2) receptor. Another indication of dendritic cell maturation is the ability to process and present antigen to antigen-specific, syngeneic T lymphocytes. Yet another indication of dendritic cell maturation is the ability to stimulate proliferation of allogeneic T lymphocytes. Still another indication of dendritic cell maturation is the ability to conjugate to T lymphocytes, particularly memory T lymphocytes. Preferably, the dendritic cells are treated with granulocyte-macrophage colony stimulating factor (GM-CSF) to induce or accelerate maturation. In addition, other cytokines, such as interleukin-1 (IL-1) increase antigen presentation function of dendritic cells and potentiate the effect of GM-CSF, e.g., on Langerhans cells.

B Cells and Lymphoblastoid Cell Lines

B cells are well known antigen presenting cells [Unanue, supra, pp. 123–124]. Antigen-specific B cells present their cognate antigen very efficiently, demonstrating as much as 100- to 10,000-fold greater efficiency compared to non-specific antigen presentation. Generally, B cells require initial activation to become competent for antigen presentation, e.g., by treatment with polyclonal activators or cytokines, including but not limited to anti-Ig and IFN-γ, by increasing expression of the B7 molecule on the B cells with T cell lymphokines such as IL-2 and IL-4, or by infection with EBV.

Preferably, EBV-transformed B cell lines are used as antigen presenting cells, either for whole virions or transduced with viral or tumor antigen expression vectors, or for endogenously expressed EBV latency-associated protein. As noted above, the present inventors have unexpectedly found that lymphoblastoid cell lines (LCLs) can effectively stimulate effector cell responses against a second virus, e.g., adenovirus or CMV, in addition to EBV. Thus, a population of effector cells specific for both EBV and another pathogen can be generated using LCLs as antigen presenting cells.

Preparation of LCLs is well known in the art [Smith et al., *J. Hematother.* 4:73–79 (1995); Rooney et al., supra; Heslop et al., supra]. Generally, autologous peripheral blood mononuclear cells (PBMCs) are plated, e.g., at about $10^6$ cells per well in flat-bottomed 96-well plates. The cells are treated with cyclosporin A alone for spontaneous transformation, or with concentrated supernatant derived from cultures of cells transformed with EBV. One example of such a culture are marmoset B cells transformed with human type 1 EBV [Miller and Lipman, *Proc. Natl. Acad. Sci. USA* 84:190 (1973); Rickinson et al, *Cell. Immunol.* 87:646 (1984)]. Once established, LCLs can be maintained in culture, e.g., in an RPMI-based culture medium, or frozen.

Mononuclear Phagocytes

Antigen presenting cells of the present invention include "mononuclear phagocyte lineage" cells, e.g., macrophages [see Unanue, supra, pp. 112–115]. Macrophages for use as antigen presenting cell in accordance with the present invention include, but are not limited to, splenic macrophages, blood-borne macrophages, bone marrow macrophages, Kupfer cells, peritoneal macrophages (e.g., elicited with peptone or thioglycollate), alveolar macrophages, microglia, and macrophages of endocrine organs.

Macrophages can be activated to present antigen, e.g, by contacting them with GM-CSF, macrophage CSF (M-CSF), granulocyte CSF (G-CSF), tumor necrosis factor (TNF)-α, TNF-β, IL-1, IL-6, IL-8, IL-12, macrophage inflammatory protein (MIP)-1α, MIP-1β, MIP-2, and interferon-γ (IFN-γ). IFN-γ is a preferred stimulatory agent to modify macrophages for stimulation of effector cells in accordance with the present invention. However, macrophages are suppressed by IL-4.

Pulsing Antigen Presenting Cells with Viral Particles

Modified antigen presenting cells can be pulsed with viral particles (i.e., virions), which are not capable of productive infection in the antigen presenting cells. Antigen presenting cells can be pulsed with virus at a multiplicity of at least 10, and preferably of at least 100; in a specific embodiment the cells are treated at a multiplicity of infection (MOI) of 100. Multiplicity varies amongst viruses. For adenovirus the range should be between 50–1000. The MOI may range up to 10,000:1. The time of treatment should be sufficient to allow uptake of the virus by the cell; preferably, the cells are exposed to viral particles for at least 30 min to one hour. The antigen presenting cells may then be irradiated, e.g., at from 1000 to 3000 cGy. Irradiation of the antigen presenting cells prevents their proliferation, thus ensuring that only antigen-specific effector cells are selected in the culture. Dendritic cells and LCLs are preferably irradiated at 3000 cGy.

As discussed above, the viral-pulsed antigen presenting cells are particularly useful for generating effector cells against immunodominant viral antigens. Accordingly, these effector cells may be useful for treating viral infections characterized by morbidity to active infectious virus or viral tumors or transformed cells in which immunodominant viral antigens are present. Examples of the former viruses include, but are by no means limited to, herpes virus, parainfluenza virus, adenovirus, cytomegalovirus, HIV-1, HIV-2, influenza virus, rabies virus, and rhinovirus. An examples of the latter include EBV in EBV lymphoproliferative disease.

A further advantage of the present invention is that it permits generation of an effector cell population specific for more than one virus. For example, using EBV-transformed LCLs as antigen presenting cells, and pulsing them with viral particles of one or more different viruses, permits generation of a population of effector cells specific for EBV and the one or more viruses. In a specific embodiment, infra, the cells are specific for EBV and adenovirus. Effector cells specific for EBV and CMV are also contemplated, as are populations of effector cells specific for EBV, CMV, and adenovirus. Multi-specific effector cells are particularly desirable for prophylactic immunotherapy, e.g., after bone marrow transplantation, since any one of these (or other) opportunistic pathogens may cause disease.

Transducing Antigen Presenting Cells with Specific Antigen Vectors

As discussed above, a significant advantage of the present invention is the ability to transduce effective antigen presenting cells, particularly dendritic cells, to express specific antigens for generating antigen-specific immune responses. As shown in the Examples, infra, a specific primary or secondary immune response against the weak EBV antigen LMP2a can be generated with LP2a-transduced dendritic cells. Similar specific responses can be generated to tumor specific antigens, including but by no means limited to prostate-specific antigen (PSA), human leukemia-associated antigen, carcinoembryonic antigen (CEA), and the melanoma-specific antigens MAGE-1 and MART-1. Thus, where effective immunotherapy requires, the present invention provides for developing an effector cell population against a selected antigen, including a weakly immunogenic antigen.

Thus, in one embodiment, the present invention is directed to the immunotherapeutic treatment of tumors, particularly solid tumors. Examples of solid tumors that can be treated according to the invention include sarcomas and carcinomas that are known or found to express a tumor specific antigen, such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. Identification of a tumor-specific antigen for such tumors, such as a papillomavirus antigen of a cervical cancer tumor, an EBV antigen of a nasopharyngeal carcinoma, HTLV-1 antigen of a T cell lymphoma, or a MAGE-1 or MART-1 antigen of a melanoma, provides a target antigen for transducing an antigen presenting cell and generating effector cells for immunotherapy.

In addition, the present invention advantageously provides for targeting latent viral infections, which can erupt in active disease, particularly latent tumor viruses. Examples of latent viral infections in which a specific viral antigen can be targeted include, but are by no means limited to, Epstein-Barr virus, papillomavirus, hepatitis A virus, hepatitis B virus, hepatitis C virus, papovavirus, HIV-1, HIV-2, human T-lymphotrophic virus (HTLV)-1, and HTLV-2. For example, a vector can be prepared to express LMP2a or papillomavirus antigen to generate a latent virus-specific cellular immune response.

The present invention requires effective transduction of the antigen presenting cells. Effective transduction means high level transduction with sufficient antigen expression to generate an antigen-specific immune response. In one embodiment, effective transduction is achieved when 30% of antigen presenting cells are transduced. Preferably, at least about 50% of the cells are transduced. More preferably, at least 60% of the cells are transduced. Most preferably, 100% of the cells are transduced, and express, process, and present the transduced antigen in the context of the class I MHC molecule. Necessarily, any immune response must be against the specific antigen, i.e., a tumor specific antigen or latent virus antigen.

Viral vectors are commonly used for ex vivo targeting and therapy procedures; these include DNA-based vectors and retroviral vectors. Methods for constructing and using viral vectors are known in the art [see, e.g., Miller and Rosman, *BioTechniques* 7:980–990 (1992)]. DNA viral vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. In addition, different viral vectors may exhibit specificity for one or another cell type. Examples of particular vectors include, but are not limited to, a defective herpes virus 1 (HSV1) vector [Kaplitt et al., *Molec. Cell. Neurosci.* 2:320–330 (1991)], defective herpes virus vector lacking a glyco-protein L gene [Patent Publication RD 371005 A], or other defective herpes virus vectors [International Patent Publication No. WO 94/21807, published Sep. 29, 1994; International Patent Publication No. WO 92/05263, published Apr. 2, 1994]; an attenuated adenovirus vector, such as the vector described by Stratford-Perricaudet et al. [*J. Clin. Invest.* 90:626–630 (1992); see also La Salle et al., *Science* 259:988–990 (1993)]; and a defective adeno-associated virus vector [Samulski et al., *J. Virol.* 61:3096–3101 (1987); Samulski et al., *J. Virol.* 63:3822–3828 (1989); Lebkowski et al., *Mol. Cell. Biol.* 8:3988–3996 (1988)]. Herpes virus vectors are preferred for dendritic cells.

In another embodiment, the gene can be introduced in a retroviral vector, e.g., as described in Anderson et al., U.S. Pat. No. 5,399,346; Mann et al., 1983, Cell 33:153; Temin et al., U.S. Pat. No. 4,650,764; Temin et al., U.S. Pat. No. 4,980,289; Markowitz et al., 1988, J. Virol. 62:1120; Temin et al., U.S. Pat. No. 5,124,263; International Patent Publication No. WO 95/07358, published Mar. 16, 1995, by Dougherty et al.; and Kuo et al., 1993, Blood 82:845. International Patent Publication No. WO 95/07358 describes high efficiency transduction of primary B lymphocytes. In a specific embodiment, infra, a Harvey murine retroviral vector is used to transduce dendritic cells. Retroviral vectors can be constructed to function as infectious particles or to undergo a single round of transfection. In the former case, the virus is modified to retain only those genes responsible for packaging and replication and to express the heterologous gene. In a specific embodiment, infra, an infectious viral vector is used. Non-infectious viral vectors are prepared to destroy the viral packaging signal, but retain the structural genes required to package the co-introduced virus engineered to contain the heterologous gene and the packaging signals. Thus, the viral particles that are produced are not capable of producing additional virus.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker [Felgner, et. al., *Proc. Natl. Acad. Sci. U.S.A.* 84:7413–7417 (1987); see Mackey, et al., *Proc. Natl. Acad. Sci. U.S.A.* 85:8027–8031 (1988); Ulmer et al., *Science* 259:1745–1748 (1993)]. The use of cationic lipids may promote encapsulation of negatively charged nucleic acids, and also promote fusion with negatively charged cell membranes [Felgner and Ringold, *Science* 337:387–388 (1989)].

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter [see, e.g., Wu et al.,*J. Biol. Chem.* 267:963–967 (1992); Wu and Wu, *J. Biol. Chem.* 263:14621–14624 (1988); Hartmut et al., Canadian Patent Application No. 2,012,311, filed Mar. 15, 1990; Williams et al., *Proc. Natl. Acad. Sci. USA* 88:2726–2730 (1991)]. However, yields of transduced cells are low with methods such as electroporation, which can also damage cells. Accordingly, these methods are not preferred with dendritic cells, which are available in limited numbers, though they may be effective with a transformed population, such as LCLs.

In a preferred embodiment, for high efficiency transduction of dendritic cells, a flow through technique can be used.

Flow Through High Efficiency Cell Transduction

Efficient gene transfer into antigen presenting cells offers a number of potential therapeutic applications. This invention modifies a "flow through" approach to cell transduction and has been able to consistently increase gene transfer efficiency into human hemopoietic progenitor cells, thus overcoming the twin problems of relatively low titre of retroviral supernatants and the requirement for cell division.

The original technique described by Chuck and Palsson [*Human Gene Therapy* 7:743–750 (1996)] consisted of passing retroviral supernatants through a porous membrane (Transwell-COL cell culture inserts from Costar), which supports target cells using gravity as the stimulus for flow. As this maneuver directs the motion of the virus it overcomes limitations of random Brownian motion, increasing the likelihood of virus-target cell interaction [Chuck and Palsson, *Biotech. Bioeng.* 51:260–270 (1996)].

This technique has been modified in the present invention by initially pulling retroviral supernatant through 0.2 micron Whatman tissue culture inserts and then placing target cells on such filters in a small volume of media. This procedure seems to result in co-localization of virus and target cells on the filter, increasing the likelihood of virus target cell interaction and productive transduction. A similar co-localization approach using fibronectin fragments has been shown to increase transduction efficiency [Hanenberg et al., *Nature Medicine* 2:876 (1996)]. Therefore the filter acts as a means to co-localize cells and virus in our modification rather than a support structure to allow directed viral motion as in the Chuck and Palsson technique.

Cells. A variety of antigen presenting cells can be used as targets including dendritic cells, B lymphoblastoid cell lines, primary B cells, macrophages, and leukemic blasts. B-LCL and EBV specific CTL lines were generated as previously described [Smith et al., *J. Hematother.* 4:73 (1995)].

Exemplary Retroviral Vectors. LNL6 or G1Na vectors (GTI, Maryland) which encode the neomycin resistance gene, and a NGFR vector, which encodes a truncated nerve growth factor receptor may be used. The neo transgene is detected by PCR or clonogenic assays in the presence of G418 [Brenner et al.,*Lancet* 342:1134, (1993); Heslop et al., *Nature Medicine* 2:545 (1996)]. The NGFR product is detected by flow cytometry. The preferred retroviral vector for dendritic cells is a Harvey murine retroviral vector (Example 2, infra).

Retroviral Transduction. In a specific embodiment, flow-through retroviral transduction can be effected as follows. An appropriate volume of retroviral supernatant to produce the desired MOI is placed on a 0.2 micron tissue culture plate insert (Anocell 25 membrane, Whatman, Maidstone. UK) sealed with surgical tape (Baxter) to a 125 ml side arm flask connected to regulated vacuum. One-half viral supernatant is left in the filter, which is transferred to a Falcon 6 well flat bottom tissue culture plate. Two ml of RPMI/FCS are added to the well outside the filter and 1 to $5 \times 10^5$ cells are placed on the virus coated membrane in 0.5 ml medium. Control transductions may be performed in conventional suspension culture in retroviral supernatant or RPMI/FCS. Transduction is performed for 6–14 hours at 37° C. in 5% $CO_2$.

Transduction of B cell lines. BLCL are efficient antigen presenting cells and transduction may allow their use to stimulate CTL specific for an antigen encoded by the transferred gene. A potential example would be adenovirus or CMV antigens.

Transduction of dendritic cells. Dendritic cells are the most potent antigen presenting cell and efficient retroviral transduction allows their use as stimulator cells to generate CTL specific for antigens encoded by the transferred gene. As these cells can also induce primary immune responses, this strategy may be particularly useful for adoptive immunotherapy approaches.

Inducing CTLs for Immunotherapy

A source of functional effector cells, comprising CTLs, provided to an immunocompromised patient may overcome vulnerability to infection. Great successes have been achieved using CTLs generated against EBV-transformed LCLs [Rooney et al., supra; Heslop et al., supra]. Effector cells can be obtained from MHC-matched donors (or from a patient prior to immunosuppression) and co-cultured with the antigen presenting cells to generate an antigen- or virus-specific effector cell population. If the subject to receive treatment is undergoing bone marrow transplantation, preferably the bone marrow donor also provides the effector cells. Since the cells are obtained from donor (or the subject), and treated outside the body prior to administration for immunotherapy, the term "ex vivo" is employed to describe the selection process.

Generally, effector cells are cultured with irradiated antigen presenting cells that have been pulsed with viral particles or transduced with a vector for expression of a specific antigen. Peripheral blood mononuclear cells (PBMCs) or peripheral blood lymphocytes (PBLs) from the donor are added to the antigen presenting cells, e.g., at a ratio of from 1:5 to 100:1, preferably 40:1. In a specific embodiment, the PBMCs are added to dendritic cells at a ratio of 2:1. In another embodiment, PBMCs are added to LCLs at a ratio of 40:1. The antigen presenting cells stimulate proliferation of antigen- or virus-specific effector cells; non-specific effector cells (CD4 and CD8 T cells) do not proliferate, and abate. Thus, the methods of the invention enrich for a population of effector cells consisting of virus- or antigen-specific cells.

Although PBMCs or PBLs are readily obtained and very easy to use as the source of effector cells, selection or isolation techniques can be used to enrich the effector population further. For example, the cells can be depleted of CD56-positive lymphocytes. Alternatively, CD3-positive cells, $\alpha,\beta$-T cell receptor-positive cells, or even $\gamma,\delta$-T cell receptor positive cells can be selected (or the latter depleted), e.g., by FACS or panning. B cells present in PBMCs or PBLs can be depleted, e.g., by panning or anti-Ig plus complement. T lymphocytes can be selected by nylon wool passage as well.

The effector cells are generally co-cultured with the irradiated APCs for about 7 to 14 days, and preferably about 10 days. Preferably, the effector cells are harvested and restimulated with fresh antigen presenting cells. At least two cycles of stimulation are necessary to get a highly enriched population of virus- or antigen-specific effector cells. Additional stimulation cycles will result in maintenance of a highly specific population of effector cells, but will not provide significantly greater specificity. Cellular immunotherapy with EBV-specific effector cells obtained after two cycles of stimulation on irradiated LCLs showed no evidence of GVH disease.

As discussed above, the effector cells generated according to the invention are useful for immunotherapy for active and latent viral infections, including but by no means limited to EBV, adenovirus, CMV, etc. CTL immunotherapy may also prove useful for the treatment of adult nasopharyngeal carcinoma (an EBV associated malignancy); for recipients of heart, heart-lung or bowel transplant (10% of whom develop EBV lymphoma); and for other transplant recipients (1–2% of whom develop EBV lymphoma). Transplant patients are also at risk for cytomegalovirus infection, a non-fatal but highly prevalent disease which should also be amenable to CTL immunotherapy. Papilloma virus, which causes laryngeal papillomatosis in infants, as well as certain head, neck and cervical cancers in adults, may also be treatable with CTL immunotherapy. AIDS patients, who are severely immunocompromised and susceptible to opportunistic infections including herpesvirus and CMV, represent another group who may be treated with CTL immunotherapy. As discussed above, either the transduced or viral particle-pulsed APCs of the invention can be used to generate a population of effector cells specific for more than one pathogen. Ideally, multi-pathogen effector cells are given prophylactically, after bone marrow transplantation, immunosuppressive therapy for organ transplantation, or chemotherapy.

The present invention may be better understood by reference to the following non-limiting Examples, which are provided as exemplary of the invention.

EXAMPLE 1
Adenovirus-Pulsed Dendritic Cells Stimulate Human Virus-Specific T Cell Responses In Vitro The present Example describes an in vitro system that permits induction and analysis of the human CTL response to adenoviruses. Cytotoxic T cells (CTLs) derived from normal donors were found to contain a mixture of effector cells that recognized virus peptides in the context of both class I or class II antigens. Endogenous viral gene expression was not required to sensitize cells to lysis by adenovirus-specific CTLs. CTLs raised against Ad5 of virus subgroup C lyse cells infected with Ad11 of subgroup B, indicating that viruses of different subgroups share common epitopes. The described system may be used to define the human immune response to adenovirus, including characterization of the viral protein(s) against which the response is generated and identification of the effector cells.

Methods

Viruses. Adenovirus type 5 dl312 (E1A$^-$) [Jones and Schenk, Proc. Natl. Acad. Sci. USA 76:3665 (1979)] and Ad5dl7001 (E3$^-$) [Ranheun et al., J. Virol. 67:2159 (1993)] were grown either on 293.1 cells (E1A$^-$), or KB spinner cells (Ad5 wild-type and E3$^-$) as previously described [Kitchingman, Virology, 212:91–101 (1995)]. Virus was purified by CsCl$_2$ density gradient centrifugation. All virus stocks were titered on 293.1 cells.

Generation and culture of dendritic cells. Peripheral blood and skin biopsy samples were obtained from four healthy adult donors. HLA types were as follows: donor CR- A2,11; B7,8; Cw$^-$; DR 15,3; donor HH- A2,3; B13,35; C4,-; DR1; donor LW- A1,1; B8,57; Cw6,w7; DR 7,17; donor GK- A1,11; B7,22; Cw3; DR1,1.

Dendritic cells were generated according to the known procedure of Romani et al. [Romani et al., J. Exp. Med. 180:83–93 (1994)]. Briefly, Ficoll-Hypaque purified peripheral blood mononuclear cells were seeded on 24-well plates (1.5 cm diameter wells) at $1\times10^6$ per well and allowed to adhere for 2 hours. Non-adherent cells were removed and frozen for later use. Adherent cells were then cultured 4 to 5 days in 800 units/ml of granulocyte-macrophage colony-stimulating factor (GM-CSF; Immunex, Seattle, Wash.) and 500 units/ml of interleukin 4 (IL-4; Peprotech, Rocky Hill, N.J.). Ten to 50% of the resulting cells exhibited the large, irregular morphology typically associated with dendritic cells. Cytofluorographic analysis revealed that these cells were CD3$^-$, CD14$^-$, CD19$^-$, HLA DR$^+$.

Generation of adenovirus-specific CTLS. The dendritic cells were pulsed with gradient-purified adenovirus in 2 ml of serum-free medium at a multiplicity of 100 for 1 hour. The dendritic cells were then irradiated (3000 cGy) and seeded into 24-well plates at $5\times10^5$ per well. The non-adherent mononuclear cells (MNCs) were then added at 1×10⁶ per well to achieve an MNC:dendritic cell ratio of 2:1. After 10 days, the co-cultures were harvested on Ficoll gradients, resuspended at 1×10⁶ per well, and re-stimulated with virion-pulsed irradiated dendritic cells, again at the ratio of 2:1. Four days later, the non-adherent cells were assayed either immediately or after 2–3 days of culture with 5–10 units/ml of interleukin 2 (IL-2; Cetus, Emeryville, Calif.).

Chromium release assay. Dermal fibroblasts were derived from skin biopsies and used as targets in cytotoxicity assays. Fibroblasts were cultured in 100 units/ml γ-interferon (Genentech, South San Francisco, Calif.) for 2 days and then infected with adenovirus at a multiplicity of infection (MOI) of 100–200 plaque forming units per cell. After 24 hours of incubation, the cells were trypsinized, labeled with $^{51}$Cr and seeded in triplicate in 96-well, flat bottomed plates at 5×10³ cells per well. The CTLs were then added at the effector to target ratio indicated in each figure for 16–18 hours before harvest of supernatants.

In several experiments actinomycin D was included to inhibit RNA transcription. Fibroblasts were incubated with 20 µg/ml of the drug for 30 minutes prior to infection. Cytotoxic T cell assays were performed exactly as described in the preceding paragraph except for the presence of actinomycin D in the medium. Brefeldin A was added in some experiments at a concentration of 1 µg/ml 30 minutes prior to virus infection, and was then present throughout the remainder of the assay at the same concentration.

Immunophenotyping and sorting. A FACScan® flow cytometer (Becton-Dickinson. San Jose, Calif.) was used to phenotype the CTL preparations. Cells were stained with pairs of monoclonal antibodies directly conjugated with fluorescein isothiocyanate or phycoerythrin which recognized the cell surface molecules CD4, CD8, CD56 (Dako, Carpinteria, Calif.), T cell receptor (TCR) γδ (Becton Dickinson, San Jose, Calif.) or TCR αβ (T Cell Diagnostics, Cambridge, Mass.), and then combined in pairs for dual fluorescence analysis. In several experiments the CTL population was depleted of CD56⁺ cells by cell surface staining and sorting on the FACStar® (Becton-Dickinson, San Jose, Calif.).

³H-Thymidine uptake experiments. Non-adherent, peripheral blood mononuclear cells were seeded in 96-well round-bottom plates at 1×10⁴ per well. Dendritic cells that were either uninfected or infected with adenovirus and irradiated were then added at the ratios indicated in the figure legends. After 10 days, ³H-thymidine was added at 10 µCi/ml and incubated for 6 hours. Cells were harvested (Harvester 96 Mach II, TomTec, Orange, Conn.) and the incorporated counts measured.

Protein and RNA gels. SDS-polyacrylamide gel electrophoresis was performed as described by Anderson et al. [Anderson et al., J. Virol. 12:241–252 (1973)]. The gels contained 12.5% acrylamide and 0.1% bisacrylamide. RNA was extracted according to the method of Chomczynski and Sacchi [Chomczynski, et al., Anal. Biochem. 162:156–159 (1987)] and probed for E2A RNA with the NarI DNA fragment of Ad5 which includes nucleotides 22612 to 23913 of the viral genome.

Results

Adenovirus-pulsed dendritic cells cause T cell proliferation. Blood dendritic cells are known to be superb antigen presenting cells [Roman et al. 1994, supra], but their permissiveness for adenovirus infection was previously unknown. Preliminary experiments using various multiplicities of infection (MOI) and staining for either adenovirus early or late proteins demonstrated that wild-type Ad5 infects 1 to 5% of the cells in the dendritic cell preparations (data not shown). To determine whether this rate of infection would be sufficient for T cell activation, normal donor mononuclear cells (MNCs) were cultured with irradiated dendritic cells that had been infected with either wild-type Ad5 or Ad5dl312, an Ad5 mutant with the E1A region deleted and consequently defective in early and late viral gene expression. On day 10, the cultures were pulsed with ³H- thymidine for 5 hours and analyzed for incorporated radiolabel. As shown in FIG. 1, the mock-infected, pulsed dendritic cells caused little or no proliferation of the MNCs. In contrast, both the wild-type and the dl312 pulsed cells induced ³H-Thy incorporation at all ratios tested. Immunophenotyping of the proliferating cells demonstrated both CD4⁺ and CD8⁺ T cells in about a 2:1 ratio. A significant minority were CD56⁺ (FIG. 1).

Adenovirus-infected dendntiic cells activate virus-specific cytotoxic T cells. The functional capability of the T cells responding to adenovirus-pulsed dendritic cells was tested by determining whether they could specifically lyse virus-infected cells. T cell lines were generated from two different donors using two rounds of stimulation. Their cell-surface phenotypes are presented in FIG. 2. The majority of responding cells were CD4⁺ T cells. The cytotoxic activity of the lines was assayed against autologous or HLA-mismatched dermal fibroblasts infected with either wild-type Ad5, dl312 (E1A⁻) or dl7001 (E3⁻). The E1A⁻ virus was included to determine whether expression of early viral genes was required to sensitize infected cells to lysis. The E3 region of the viral genome is responsible for downregulating expression of the MHC complex on the infected cell surface (reviewed in Gooding and Wold, Crit. Rev. Immunol., 10:53–71 (1990), Wold and Gooding, Virology, 184:1–8 (1991)) and in its absence in dl7001 would be expected to allow higher levels of class I expression. The results are shown in FIG. 2. Neither of the donor-derived T cell lines significantly killed uninfected fibroblasts. In contrast, both T cell lines killed infected cells, regardless of whether the targets were infected with wild-type Ad5, E1A⁻, or E3⁻. However, the susceptibilities of the targets varied markedly. For donor CR, E3⁻-infected targets were more susceptible than E1A⁻-infected targets which, in turn, were more susceptible than wild-type-infected targets. Killing of the autologous infected targets was consistently greater than the killing of the mismatched infected targets over the entire range of effector-to-target ratios tested. This suggested that much of the cytolytic activity of the T cells was HLA-restricted, a hallmark of CTLs which recognize antigen presented via class I or II molecules.

Figure 3:
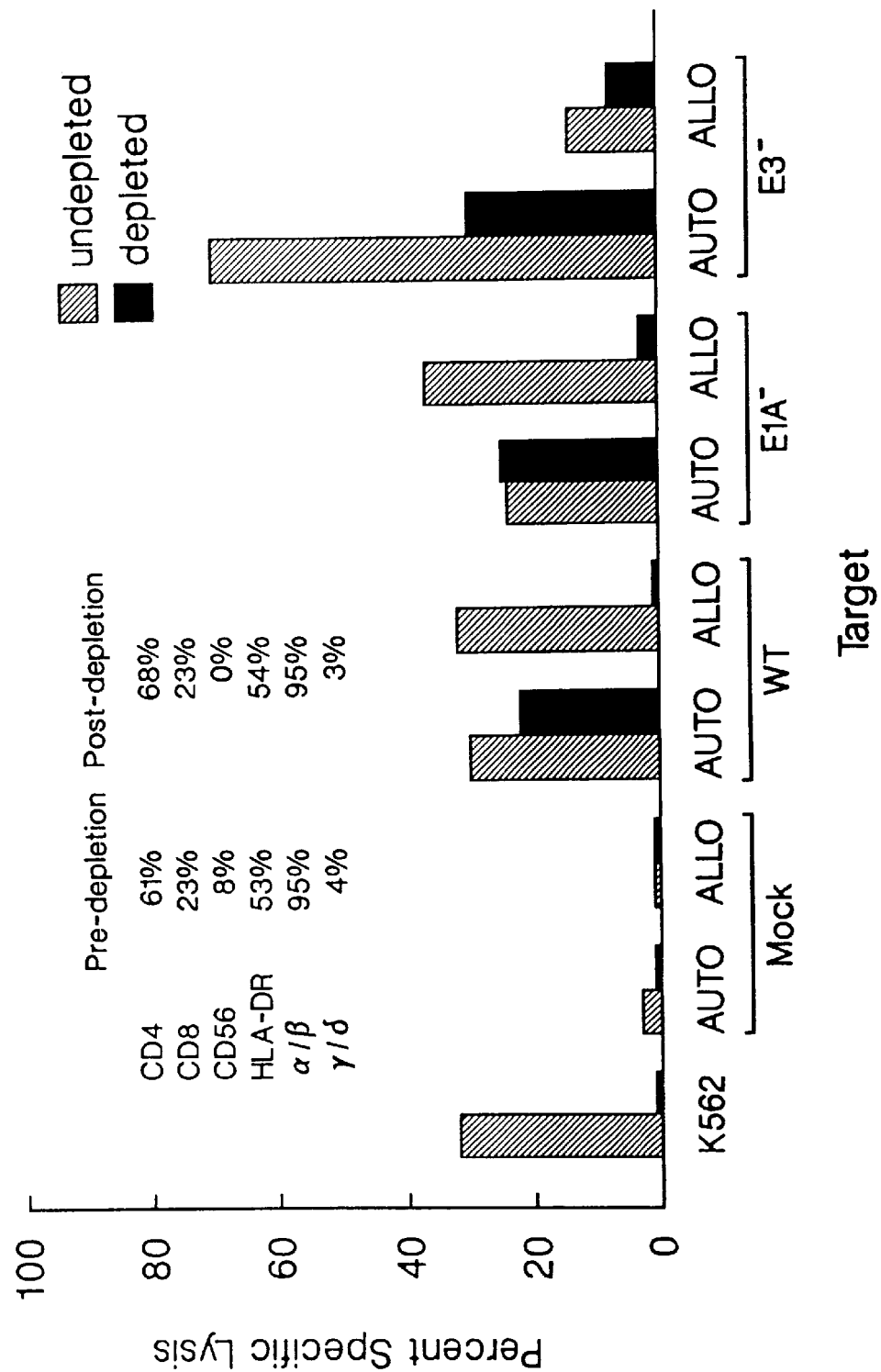
FIG. 3. Cytotoxicity of CD56$^+$-depleted versus non-depleted CTLs. CD56$^+$-depleted (solid bars) and non-depleted (cross-hatched bars) CTLs were prepared from LW and assayed against either uninfected K562 cells or against autologous (AUTO) or allogeneic (ALLO) fibroblasts either mock infected or infected with the indicated viruses. The relative populations before and after depletion are listed in the figure.

In FIG. 2, the results showed that a higher than background level of killing of the HLA-mismatched, infected targets was present, particularly with T cells generated from CR when assayed against E3⁻-infected cells. This suggested that adenovirus-pulsed dendritic cells also stimulated the proliferation of HLA-unrestricted killers. To test this hypothesis, we depleted CD56⁺ cells from an aliquot of CTLs from donor HH. CD56 is a cell-surface molecule expressed by HLA-unrestricted killer T cells. Depleted and undepleted aliquots were then assayed against a variety of infected and uninfected targets. As shown in FIG. 3, the undepleted T cells killed K562, an immortalized erythroleukemia cell line particularly sensitive to HLA-unrestricted killers. In contrast, the depleted aliquot failed to lyse this target, thus confirming that the unrestricted killing was mediated by an NK-type cell. When assayed against virus-infected fibroblasts, the CD56⁻ cells did not kill HLA-mismatched targets significantly. However, the depleted aliquot retained its ability to lyse the matched, infected targets. Thus, adenovirus-infected dendritic cells produced both HLA-restricted and unrestricted T cell populations.

Figure 4:
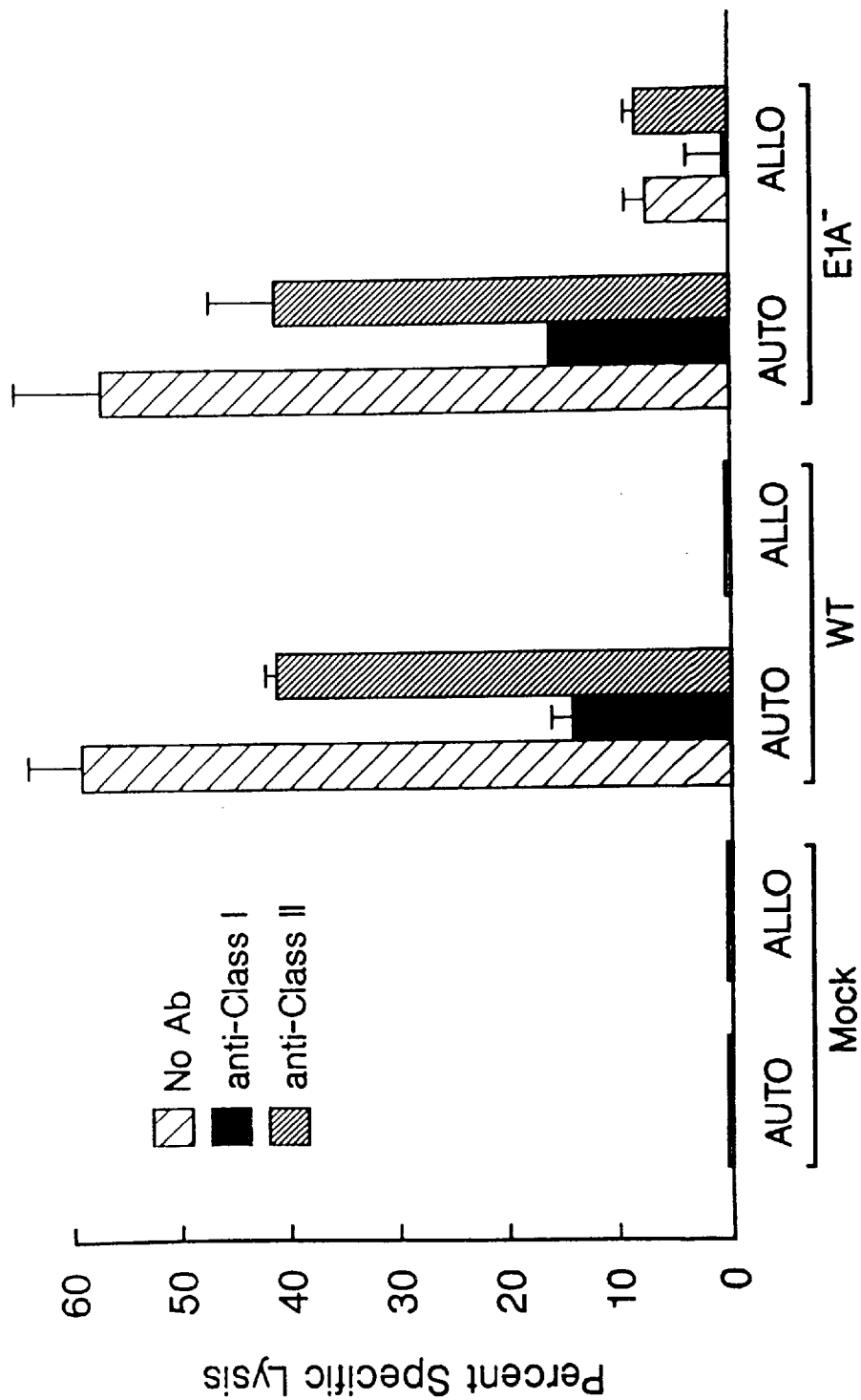
FIG. 4. The effects of blocking antibodies specific for HLA-A,B,C (class I, solid bar) or HLA-DR (class II, dense diagonal bar) on lysis of infected fibroblasts mediated by CD56$^+$-depleted CTLs. Control cells (open diagonal) were not treated with antibody. As indicated, fibroblasts were either left uninfected (mock) or infected with either Ad5 (WT) or dl312 (E1A−). Both autologous (AUTO) and HLA-mismatched (ALLO) fibroblasts were used as targets.

The CTL preparations consisted of both CD4⁺ and CD8⁺ cells, and killing could potentially be mediated either through class I or II antigens. CD56⁺-depleted, adenovirus-specific CTLs were assayed against virus-infected targets in the presence or absence of blocking antibodies directed against monomorphic determinants of either HLA-ABC (class I MHC) or HLA-DR (class II MHC). As shown in FIG. 4, both antibodies inhibited the CTL-mediated killing. Importantly, when the percentages of suppression observed with each antibody were summed, the result was nearly 100%. To confirm these results, CTL preparations were sorted into CD4⁺ and CD8⁺ populations, and examined for their ability to kill virus-infected fibroblasts. The results demonstrate that pure populations of both the class I-restricted CD8⁺ cells and class II-restricted CD4⁺ cells could kill autologous infected fibroblasts. Collectively, these results indicate that both class I and II molecules present antigen to adenovirus-specific CTLs.

Expression of virus proteins in fibroblasts infected with adenovirus mutants. The killing of the E1A⁻ virus-infected fibroblasts was unexpected, since this mutant should not express virus genes de novo. However, at high MOIs or in certain cell types, E1A⁻ viruses can replicate [Horwitz, *Virology,* 2:1679–1721, (1990)], so we examined E1A⁻-virus infected fibroblasts to determine if under the conditions used that virus proteins were being synthesized. Both the wild-type virus and the E3⁻ virus produced a broad array of viral proteins following infection of primary fibroblasts, including the hexon molecule, a prototypical late viral protein. This result was not surprising since the E3 region is not essential for any aspect of viral gene expression in tissue culture [Horwitz, 1990, supra]. In contrast, no viral protein synthesis was detected in fibroblasts infected with the E1A⁻ virus (data not shown). Northern blot analysis of RNA extracted from these cells did not reveal any detectable early viral RNAs (data not shown). The E1A region deleted in dl312 is required for early and late viral gene expression [Routes and Cook, *J. Immunol.* 144:2763–2770 (1990)] and cells infected with this virus would not be expected by synthesize viral RNAs. Recognition of fibroblasts infected with the E1A⁻ virus indicates that de novo viral gene expression is not required for CTL killing.

Endogenous viral gene expression is not required to sensitize fibroblasts to lysis by adenovirus-specific, HLA-restricted T cells. The sensitivity of the E1A⁻-infected cells to lysis by CTLs suggested that the inoculum itself rendered cells susceptible to killing. To further test this hypothesis, adenovirus-specific CTLs were assayed for their ability to kill E1A⁻ virus-infected fibroblasts in the presence of actinomycin D. Such treated targets are doubly blocked for de novo viral gene expression as actinomycin D inhibits mRNA synthesis at the level of transcription. As shown in FIG. 5, the drug had no effect on infected target cell lysis mediated by the virus-specific CTLs. This result suggested that fibroblasts process absorbed virion protein in such a way that they become targets for CTL-mediated lysis without the need for de novo viral gene expression.

CTLs generated against Ad5 lyse targets infected with Ad11. There are around 50 adenovirus serotypes classified into six subgroups, and there is evidence from work in rodent systems that cellular immunity against one subgroup will not protect against infection by another. To determine if this were true for humans also, CTLs against Ad5 (subgroup C) were assayed against fibroblasts infected with Ad11 (subgroup B). These CTLs readily killed fibroblasts infected with either the homologous virus or Ad11 (FIG. 6). The almost complete absence of killing of the mismatched fibroblasts indicated that this killing was not due to NK cell activity. Thus, at least some of the antigenic epitopes recognized by adenovirus-specific CTLs appear to be conserved among subgroups.

Discussion

The present example shows that adenovirus-specific cytotoxic T lymphocytes from normal adults can be grown in vitro. T cells from all donors tested mounted strong cellular responses to adenovirus-pulsed dendritic cells. This likely represents a secondary immune response as almost all adults have experienced a group C adenovirus infection during childhood and therefore have memory B and T cells [Smitz et al., *Am. J. Epidemiol.* 117:455–466 (1983)]. Both HLA-restricted and HLA-unrestricted CTLs responded to the infected antigen-presenting cells. Removal of the unrestricted component by depleting cells positive for CD56 (FIG. 3) suggested that unrestricted CTLs were NK or lymphokine-activated killer cells. This dual response has been observed previously when human polyclonal CTLs were generated in vitro against viral antigens [Smith et al., *Br. J. Hematotherapy* 4:73–79 (1995)]. The instant Example also demonstrates cross-reactivity of the adenovirus-specific CTLs, as CTLs generated against a subgroup C adenovirus recognized and killed cells infected with a subgroup B adenovirus.

Dendritic cells were chosen as adenoviral antigen presenting cells (APC) because they are efficient APCs and are relatively easily enriched [Romani et al., *J. Exp. Med.* 169:1169–1174 (1989); Romani et al., 1994, supra]. The present Example demonstrates that dendritic cells can process and present antigen derived from the input virus inoculum itself in the context of the class I MHC molecule without a requirement for viral gene expression. The finding that dendritic cells are able to process virus capsid proteins was not expected, but it is consistent with studies showing that dendritic cells can process and present exogenously provided whole proteins to CD8⁺ T cells on HLA class I molecules, as well as small peptides [Romani et al., 1989, supra]. The present results, showing that de novo viral protein synthesis in the target fibroblasts was not required for recognition by CTLs, are similar to the finding that de novo viral protein synthesis is not required for efficient antigen presentation in cytomegalovirus-infected fibroblasts [Riddell et al. *J. Immunol.* 146:2795–2804 (1991)], although there are clearly differences between exogenously added virus and infective virus. Using dendritic cells for antigen presentation, as in the present Example, Bender et al. [Bender et al., J. Exp. Med. 182:1663–1671 (1995)] demonstrated that inactivated influenza virus could elicit CD8⁺ CTL responses. In conjunction with the results indicated in the present Example, these data collectively provide strong support for the hypothesis that virus capsid proteins from the inoculum serve as a source of antigen for presentation, and that the antigens are processed inside of the cell.

The CTLs generated in vitro recognize the same class of antigens as CTLs taken from immune individuals, that is, capsid antigens. One concern in using an in vitro system for generating a cellular immune response against adenovirus was that it would not mimic the in vivo response to a normal infection. In vivo, fibroblasts and epithelial cells are the targets for adenovirus infection, while the present Example uses dendritic cells, which are not efficiently infected by adenovirus as APCs in vitro. Recently, it was demonstrated that either adenovirus antigens or whole virus is capable of stimulating human peripheral blood MNCs from healthy donors, and that the majority of the responding cells were CD4$^+$ [Flomenberg et al., *J. Infect. Dis.* 171:1090–1096 (1995)]. This result is consistent with the hypothesis that viral capsid proteins are the targets of CTLs. Moreover, there was specific recognition of late adenoviral proteins by T cells from normal donors by using purified viral antigens bound to nitrocellulose [Souberbielle and Russell, *J. Infect. Dis.* 172:1421–1422 (1995)]. The most significant responses were directed against the fiber and protein VI, and to a lesser extent against hexon. One difference between the results of the present Example and those of Flomenberg et al. [Flomenberg et al., 1995, supra] is that while in both studies the phenotype of the majority of the responding cells was CD4$^+$, the instant have demonstrated that the majority of the cytotoxic activity is found in the CD8$^+$, class I MHC restricted, fraction (FIG. 4). This implies that the TAP transport system plays a role in viral antigen processing and presentation [Hill and Ploegh, *Proc. Natl. Acad. Sci. USA* 92:341–343 (1995)]. Collectively, the human data for adenovirus indicate strongly that there is a considerable response by T cells to the viral capsid proteins, a result that clearly contrasts with the work to date in the mouse. However, the results are consistent with those from similar studies with other human DNA viruses such as CMV [Riddel et al., *Sciences* 257:238–241 (1992)] and herpes simplex virus [Tigges et al., *J. Virol.* 66:1622–1634 (1992)]. In all cases, the cellular immune system can present viral capsid antigens without the need for productive infection. Recognition of processed capsid antigen potentially would allow rapid cytolysis of infected cells before the assembly of virions could occur.

The differences between the immune response of humans and rodents to adenovirus infection may either reflect the differences in the in vitro and in vivo systems employed, or may reflect true differences in the pathology of infections in a natural versus unnatural host. The major CTL response against adenovirus-infected rodent cells is directed against early viral proteins [Pereira et al., *Virology,* 211:268–277 (1995); Routes et al., *J. Virol.* 65: 1450–1456 (1991), Routes et al. *J. Virol.* 67:3176–3181 (1993)], while in humans it is against capsid antigens [Flomenberg et al., 1995, supra; Souberbielle and Russell, 1995, supra]. The form in which the adenovirus proteins are administered to rodents does not seem to matter, as early proteins are the targets for CTLs when the animals are either immunized with adenovirus transformed, syngeneic cells [Routes et al., 1993, supra] or with replication competent virus [Routes et al, 1991, supra].

However, some similarities do exist. Class I-restricted CTLs play a major role in eliminating adenovirus-infected cells in rodents, as shown by using transgenic mice lacking components of this pathway [Yang et al., *Proc. Natl. Acad. Sci. USA,* 92:7257–7261 (1995)], and our results show that the majority of the killing of adenovirus-infected human cells is mediated by CD8$^+$ cells (FIG. 4). NK activity against adenovirus-infected cells in rodents is high [Routes and Cook, 1990, supra], and while others have found little response by NK cells to adenovirus-infected human cells [Routes and Cook, 1990, supra], the present results show significant levels of HLA-unrestricted killing which is due to the CD56$^+$ cells in the population (FIG. 3). It is not clear whether in humans the target of the immune response differs depending on the HLA type, as is the case in mice where some respond to E1A, while other mice respond principally to E2A [Müullbacher et al., *Immunol. Cell Biol.,* 67:31–39 (1989); Rawle et al., *J. Immunol.* 146:3977–3984 (1991)].

The E3-deleted adenovirus was included in this study because it lacks a region of the viral genome that encodes a variety of proteins that decrease the infected cell's susceptibility to lysis by CTLs and tumor necrosis factor [Gooding and Wold, 1990, supra; Wold and Gooding, 1991, supra]. Predictably, dl7001-infected fibroblasts were more susceptible to CTL-mediated killing with some donors (FIG. 2), a result consistent with the fact that the virus is deleted for a gene encoding a glycoprotein that interferes with class I antigen expression on the cell surface [Wold and Gooding, 1991, supra]. Cells from donor LW showed no increased susceptibility when the E3$^-$ virus-infected fibroblasts were used as a target, whereas large differences were found for infected fibroblasts from another donor, HH (data not shown). Cells from donor CR showed an intermediate effect (FIG. 2). This is potentially due to the difference in binding affinity of various class I molecules for the E3/gp19K protein [Beier et al., J. Immunol. 304:3862–3871 (1994)]. HLA-A2.1 and -B7 bind very well to gp19K, and donors CR and HH have at least one of these alleles. HLA-A1 binds gp19K less tightly than -A2.1 and -B7 and donor LW, whose fibroblasts showed no difference in susceptibility to killing when infected with the E3-deleted virus, is homozygous for this allele. The instant data are consistent with the known binding affinities of gp19K and HLA alleles, but it may be premature to ascribe the differences in sensitization we see with and without E3 solely to this interaction. It is still unknown which viral peptides are presented to CTLs and which HLA proteins do the presenting, and further work in this area is necessary.

CTLs raised against Ad5 lyse fibroblasts infected with Ad11. Ad5 and Ad11 belong to subgroups C and B, respectively [Bailey et al., Virology 205:438–452 (1994)]. By definition, antisera raised against members of one subgroup do not neutralize the infectivity of members of any other subgroup. Consequently, the finding that CTLs raised against one serological subgroup can cross-react with viruses of another is surprising (FIG. 6). However, similar conclusions were reached in that individuals who were seronegative for previous exposure to the subgroup B adenovirus type 35 were nevertheless able to mount a vigorous proliferative response to the virus in vitro [Flomenberg et al., 1995, supra]. All of these individuals were seropositive for antibodies to Ad2, and these authors concluded that there were cross-reactive epitopes in the Ad2 and Ad35 capsids [Flomenberg et al., 1995, supra]. These results stand in contrast to the finding that murine Ad5-specific CTLs do not kill cells infected with viruses of different subgroups [Routes et al., 1991, supra]. The reason for this difference is not clear, but could be related to the possible difference in identity of the virus proteins recognized by human or mouse CTLs. The fact that human CTLs are cross-reactive has important practical consequences, especially in regard to developing adenovirus-specific CTLs for human therapy. Unselected donor lymphocytes have been used successfully in a single case to treat an adenovirus infection following bone marrow transplantation [Hromas et al., Blood, 84:1689–1690 (1994)], and infusions of either donor leukocytes [Wold and Gooding, 1991, supra] or virus-specific clones [Rooney et al., *Lancet,* 345:9–12 (1990); Walter et al., *New Engl. J. Med.,* 333:1038–1044 (1995)] have been used to treat infections of other viruses in immunocompromised individuals. The present results for adenovirus suggest that treatment and/or prophylaxis may be achievable using CTLs prepared against a single subgroup, an important point given that adenoviruses from most subgroups can cause infection in transplant patients [Flomenberg et al., *J. Infect. Dis.*, 169:775–781 (1994)].

The fact that input virus generates an immune response is significant, especially in view of the increasing use of replication-incompetent adenovirus for human gene therapy. The strong reaction of the immune system observed following the use of the current generation of adenovirus-based gene therapy vectors may not be significantly diminished by using viral vectors either with additional mutations [Yang et al., *Nature Genet.*, 7:362–369 (1994)] or vectors derived from different subgroups. Data of the present Example suggest that such vectors will be immunogenic even if they are entirely transcriptionally silent. Identification and characterization of the viral proteins recognized by human CTLs and definition of the epitopes may lead to the design of vectors capable of escaping a memory T cell response.

The present invention may be better understood by reference to the following non-limiting Examples, which are provided as exemplary of the invention.

EXAMPLE 2
Gene-modified Dendritic Cells Induce Both Primary and Memory Immune Responses Epstein-Barr virus associated neoplasms demonstrate differential expression of the virus-associated latency proteins which are targets for immune attack. The tumor cells of post-transplant lymphoproliferative diseases express 9 latent proteins, EBNA1, 2, 3a, 3b, 3c, -LP, LMP1, 2a and 2b, which are highly immunogenic, survive only in the immunocompromised host and can be eradicated with virus-specific CTLs. Other neoplasms, such as Hodgkin disease, express only the weakly immunogenic proteins EBNA1, LMP1, and LMP2a. A low frequency of CTL precursors (CTLp) to these proteins could explain tumor persistence in an immunological normal host. To activate low frequency or low affinity CTLps, LMP2a is expressed in autologous dendritic cells (DC) using a retrovirus and a reverse-flow-through transduction method. This method produces 60% LMP2a-expressing DC which can subsequently stimulate LMP2a-specific CTLs from EBV-seropositive donors as assessed by cytotoxicity assays using autologous fibroblasts expressing LMP2a. By contrast, when the EBV-transformed B cell line is used as an antigen presenting cell (APC) no discernible LMP2a reactive precursor cells are activated. This technique was also used to generate LMP2a-specific CTLs from EBV-seronegative donors. Hence, not only can this approach be used to generate memory responses against weakly immunogenic tumor-associated antigens, it can also be used to generate in vitro immune responses in naive hosts. This method may also prove beneficial in generating CTLs for the treatment of other malignancies which express specific viral or tumor antigens.

Methods

Culture of dendritic cells from peripheral blood. Dendritic cells (DCs) were prepared from peripheral blood using the known method of Romani et al. [*J. Exp. Med.* 180:83–93 (1994)]. Briefly, 40–120 mls of peripheral blood were obtained from healthy volunteers. Peripheral blood mononuclear cells (PBMCs) were isolated by Lymphoprep (Nycomed, Oslo, Norway) separation, washed and resuspended in RPMI 1640 medium (GIBCO Life Technologies, Grand Island, N.Y.) supplemented with 10% fetal bovine serum (Hyclone, Logan, Utah), 100 units per ml of penicillin, 100 mg per ml of streptomycin and 1 mM L-glutamine (Biowhittaker, Walkersville, Md.). Two mls of cells at $1-2\times10^6$ cells per ml were plated per well in flat-bottomed 24-well plates (Costar, Cambridge, Mass.). After 2 hrs of incubation at 37° C., 5% $CO_2$, the non-adherent cells were removed by gentle pipetting and the adherent cells were cultured in supplemented RPMI 1640 containing 800 units per ml of GM-CSF (SARGRAMOSTIM LEUKIN™, Immunex Corporation, Seattle, Wash.) and 500 units per ml of interleukin 4 (Endogen, Cambridge, Mass.). The cells were fed with supplemented RPMI 1640 containing 800 units per ml of GM-CSF every 2–3 days, and after 5 or 6 days in culture the DCs were FACS sorted.

Retrovirus transduction of human dendritic cells. Retrovirus-mediated gene transfer was performed using a modified flow-through transduction method [Chuck and Palsson, *Human Gene Ther.* 7:743–750 (1996)]. Briefly, DCs at $3-4\times10^4$ per ml were resuspended in supplemented RPMI 1640 containing 800 units per ml of GM-CSF. Before use, the Bing HaLMP2A was filtered through a 0.45 μm pore-sized filter (Coster, Cambridge, Mass.). A tissue culture plate insert, Anocell 25 membrane with a pore size of 0.2 μm (Whatman, Maidstone. England), was securely sealed with surgical tape on to the top of a 125 mls sidearmed flask and the apparatus attached to a vacuum device (Ohmeda, Columbia, Md.). Thirty to forty mls of viral supernatant (estimated titer: $1\times10^4$ pfu per ml) was passed through the membrane applying 40–60 mmHg vacuum. Once all the supernatant was through, 1 ml of resuspended DCs was applied to the virus-loaded membrane and the vacuum reapplied at 20 mmHg for another 5–10 minutes until all cells were firmly on the membrane surface. The membrane was placed in a 6-well plate (Costar, Cambridge, Mass.) with 5 mls of complete media containing GM-CSF. After 16 hrs in culture, the DCs were harvested from the filter, washed in RPMI 1640 twice and resuspended in fresh media. After 48 hrs the cells were analyzed for retroviral integration.

Generation of LMP2A specific CTLs. LMP2A-specific CTLs were prepared by stimulating donor's lymphocytes with autologous HaLMP2A transduced DCs. PBMCs were plated in supplemented RPMI 1640 in flat-bottomed 24-well plates at $2\times10^6$ cells per well and stimulated with $5\times10^4$ irradiated (40 Gy) autologous HaLMP2A transduced DCs. After 10 days of co-culture, the cells were harvested, subcultured in flat-bottomed 24-well plates at $8\times10^5$ cells per well and restimulated with $2\times10^5$ per well of irradiated transduced DCs. After 17–21 days, the cultures were fed with 20 units per ml of interleukin-2 (IL-2: Proleukin, Cetus, Emeryville, Calif.). Thereafter the cultures were fed 3 times weekly, twice with 20 units per ml of IL-2 and the third time with 20 units per ml of IL-2 supplemented with irradiated transduced DCs at a T cells to DCs ratio of 4:1. After 3 stimulations with HaLMP2A transduced DCs, autologous irradiated EBV-transformed lymphoblastoid cells (LCLS) were used instead. To increase the rate of expansion, cell lines were given a mitogenic booster consisting of $10\times10^5$ irradiated (30 Gy) allogeneic CMV-negative PBMCs, $1\times10^5$ irradiated (40 Gy) LCLS, 20 units per ml of IL-2 and 50 ng per ml of OKT3 (Orthodiagnostics, N.J.) but not before day 21 of culture to avoid stimulating allospecific clones.

Analysis of LMP2a gene integration and expression on dendritic cells. Total cellular RNA was isolated from transduced DCs using RNeasy total RNA kit (Quiagen, Chatsworth, Calif.). Two hundred ng of extracted RNA was treated with DNase I and then cDNA synthesis was performed for 30 minutes at 42° C. with Molony murine leukemia virus RTase (GIBCO BRL) using 13 pmol of a 3' primer specific for LMP2a mRNA that sequence was as follows: 5'-CATGTTAGGCAAATTGCAAA-3'(SEQ ID NO:1), followed by 5 minutes of heating at 99° C. Samples were then subjected to 40 rounds of amplification in a DNA thermal cycler (Perkin-Elmer Cetus) in a volume of 100 μL. Each cycle consisted of denaturing for 1 minute at 94° C., annealing for 1 minute at 55° C. and extension for 0.5 minute at 72° C. The 5' primer sequence was as follows: 5'-ATGACTCATCTCAACACATA-3'(SEQ ID NO:2). This reaction amplified a 280 bp segment of the gene. Twenty-five microliters of the PCR-amplified products were analyzed by gel electrophoresis (2.5% agarose) followed by Southern blotting using a radio labeled probe specific for the LMP2a gene. RNAs from LCLS and HSB-2 cells were used as positive and negative controls, respectively.

Generation of EBV-transformed B cell lines. The stimulator cells used to generate the EBV-specific CTLs were EBV-transformed lymphoblastoid cells (LCLS) prepared from patient's peripheral blood mononuclear cells (PBMCs). PBMCs ($5 \times 10^6$ cells) were plated in flat-bottomed 96-well plates in RPMI 1640 medium (GIBCO Life Technologies, Grand Island, N.Y.) containing 10% fetal bovine serum (Hyclone, Logan, Utah), 100 units per ml of penicillin, 100 μg per ml of streptomycin and 1 mM L-glutamine (Biowhittaker, Walkersville, Md.), and 1 μg per ml of cyclosporin A (Sandoz) with 10 μl of concentrated supernatant derived from the B95-8, a marmoset B cell line transformed by human type 1 EBV, in a total of 200 μl medium. Cells were fed weekly with complete media until lines were established. Once B95-8-infected LCLS were established, they were expanded into 25 cm$^2$ flasks for long-term culture.

Generation and expansion of EBV-specific cytotoxic T cell lines. EBV-specific CTLs were prepared by stimulating patient's lymphocytes with autologous LCLS. PBMCs were plated in supplemented RPMI 1640 in flat-bottomed 24-well plates at $2 \times 10^6$ cells per well and stimulated with $5 \times 10^4$ irradiated autologous LCLS (ratio 40:1). After 10 days of co-culture, the cells were harvested, subcultured in flat-bottomed 24-well plates at $8-10^5$ per well, and restimulated with $2 \times 10^5$ per well of irradiated LCLS. After 17–21 days in culture, the cultures were fed with 20 U/ml of IL-2 (Proleukin, Cetus, Emeryville, Calif.). Thereafter, the cultures were fed three times weekly, twice with 20 U/ml of IL-2 and the third time with 20 U/ml of IL-2 supplemented with irradiated LCLS at a T cell to LCL ratio of 4:1. To increase the rate of expansion, cell lines were given a mitogenic boost consisting of $5 \times 10^5$ irradiated (30Gy) allogeneic CMV-negative PBMCs, $1 \times 10^5$ irradiated (40Gy) LCLS, 20 U/ml IL-2 and 50 ng/ml OKT3 (Ortho Diagnostics, Raritan N.J.), but not before day 21 of culture to avoid stimulating allospecific clones.

Figure 7:
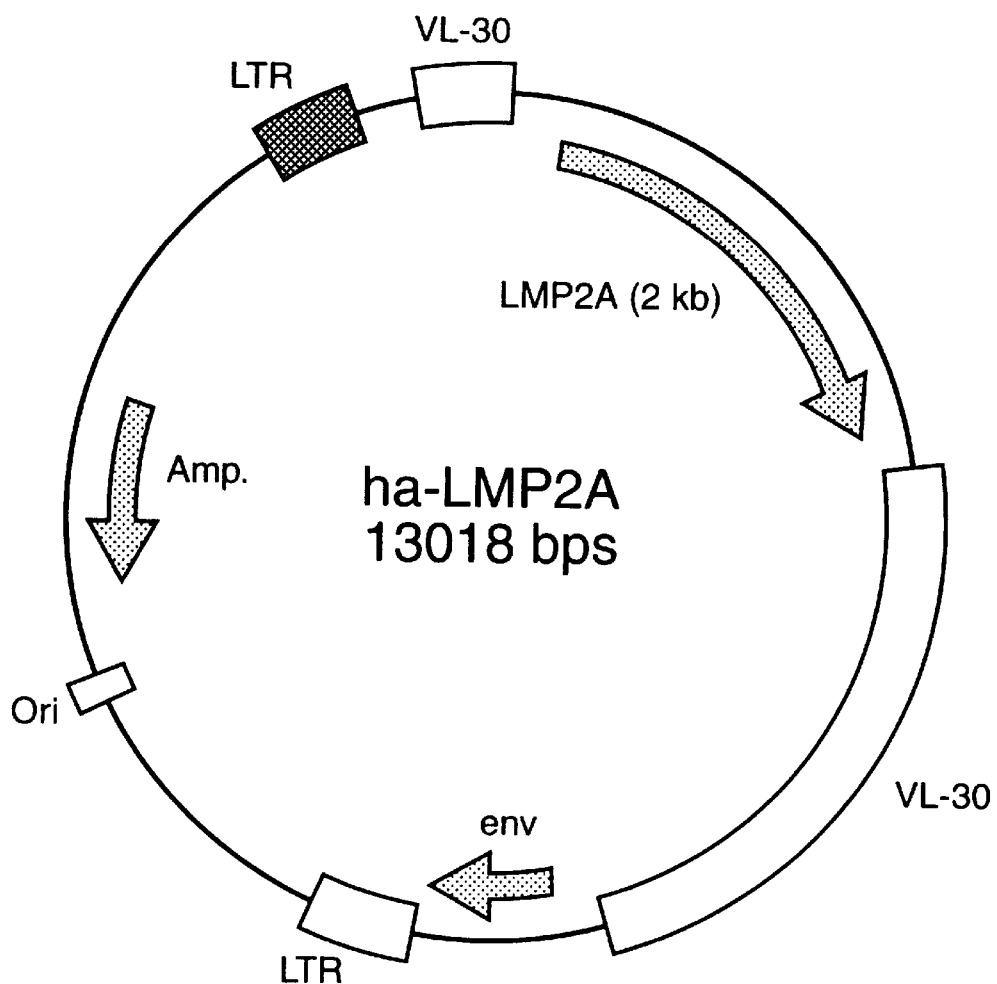
FIG. 7. Harvey murine leukemia retroviral backbone containing the full length LMP2A cDNA driven by the LTR promoter.

Generation of retroviral recombinant. The full length LMP-2a gene [Sample et al., *J. Virol.*, 63:933 (1989)] was cloned into the vector Bluescript pBS (Pharmingen) at the EcoR1 site. This plasmid was digested with PstI and SmaI and tLMP-2a fragment, now minus the polyadenylation signal and tail, extracted and gel purified. A plasmid pSL 1180/LMP-2a was constructed by cutting the vector pSL 1180 (Stratagene) with PstI and SmaI and ligating the purified LMP-2a fragment into the backbone. This construct was digested with XhoI and SacII and the LMP-2a containing fragment extracted and gel purified. Finally, this LMP-2a fragment was ligated into the Harvey murine retroviral backbone [Fichelson et al, *J. Immunol.*, 154:1577 (1995)] which had been digested with XhoI and SacII. This final 13,018 bps construct, referred to as Ha-LMP2a (FIG. 7), contained an ampicillin resistance gene and the full length LMP-2a gene which was driven by the LTR promoter.

Retroviral supernatant production. Bing producer cells were seeded at $2.5 \times 10^6$ per 60mm plate in 4 mls of DMEM (GIBCO Life Technologies, Grand Island, N.Y.) containing 10% fetal calf serum (Hyclone, Logan, Utah), 18–24 hrs prior to transfection. Immediately prior to transfection, the media was changed to 4 mls of DMEM containing 10% FCS and 25 uM chloroquine (Sigma Chemicals, St Louis, Mo.). The cells were transfected by adding 20 μg of HaLMP-2a DNA to $CaCl_2$ (2.5M)/$H_2O$ in a total volume of 500 μl. To this was added 500 μl of 2× Hepes buffered saline (GIBCO Life Technologies) pH=7.08 whilst vortexing vigorously. After 10 hrs, this media was replaced with 2.5 mls of DMEM containing 10% FCS, 1 MM L-glutamine 100 units per ml of penicillin and 100 μg per ml of streptomycin (Biowhittaker, Walkerville, Md.). After 24 hrs, the retrovirus containing supernatant was removed, filtered and stored at −70°. This process of collecting supernatant was repeated after 48 hrs.

FACS sorting of dendritic cells. After 5–6 days in culture, a purified population of dendritic cells was obtained by FACS sorting (Becton-Dickinson, San Jose, Calif.). The cells were washed twice in 1× phosphate buffered saline containing 2% human albumin (GIBCO Technologies). The cell pellet was resuspended in 50 μl of normal rabbit serum per $10^6$ cells and incubated for 20 minutes at room temperature. The antibodies were then added directly to the incubated cells. Ten μl of CD1a (Coulter, Miami, Fla.) per $10^6$ cells and $10^6$ HLA class II antibody (Becton-Dickinson) were used. For the isotype control mouse pure IgG1 (10 ul per $10^6$ cells) and mouse pure IgG2a (10 ul per $10^6$ cells) were used. The cells were incubated for 10 minutes at room temperature before washing twice with buffered PBS. Both cell pellets from isotype control and sample were resuspended in 4 μl per $10^6$ cells of both rat anti mouse IgG1-FITC and IgG2a-RPE (Becton-Dickinson) and incubated at room temperature for 10 minutes in the dark. The cells were finally washed in buffered PBS before being sorted. Cells which were both CD1a and MHC class II positive were selected.

Cytotoxicity assays. Recombinant vaccinia virus vectors coding for each of the EBV latent proteins (EBNA-1, EBNA-2, EBNA-3a, EBNA-3B, EBNA-3C, LMP-1, and LMP-2A) and a control vacc-bGal have all been previously described. For cytotoxicity assays, autologous skin fibroblasts were infected for 2 hrs with recombinant vaccinia virus at a multiplicity of infection of 10:1. These cells had been incubated in IFN (100 u/ml) for the preceding 48hrs. After viral infection, they were labelled for 1 hr with $^{51}CrO_4$, washed and incubated with CTLs in a standard 4 hr chromium release assay at Known target/effector ratios. The other targets used were autologous and mismatched LCLS and the LAK-sensitive cell line, HSB2. Prior to harvesting, the plates were centrifuged and 100 μl of supernatant was collected to measure radioactivity. Percent specific release was calculated as (experimental release—spontaneous release)/(maximum release—spontaneous release)×100. Each assay was performed in triplicate.

Cell proliferation assay. Peripheral blood mononuclear cells were seeded in 96-well plates at $2.5 \times 10^5$ per well. Dendritic cells either transduced with HaLMP2A or Harvey backbone alone were irradiated (4000 rad) and added at a ratio of 2:1. After 3, 5, and 10 days, ($^3$H) Thymidine was added at 10 uCi/ml and incubated for 6 h. Cells were harvested and the incorporated counts were measured. Assays were performed in triplicate and LCLS were used as a positive control.

Results

Dendritic cells are efficiently transduced with an LMP-2A-containing retrovirus. A wide variety of both viral and non-viral transduction methods were tested for their ability to stably and efficiently transduce human dendritic cells. The purpose of the present Example was to develop a method which would be highly reproducible, efficient and non-cytotoxic on previously frozen cells. These criteria are of importance if transduced dendritic cells are to be used in clinical application. Retroviral gene transfer using a vacuum-assisted flow through device, best fit these criteria. Therefore, an LMP2A-containing retrovirus was constructed by cloning the full length LMP2A gene into the Harvey murine leukemia retroviral backbone (FIG. 7), and employed to generate transient retrovirus-containing supernatants using the amphotrophic Bing cell producer system.

Figure 8A:
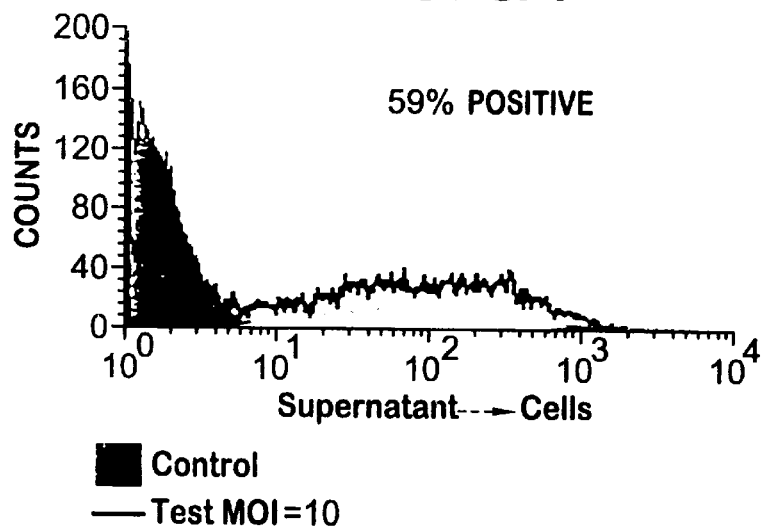
FIGS. 8A–8C. FACS analysis of Retroviral transduction of dendritic cells using the vacuum assisted reverse-flow-through transduction method and a reporter retroviral construct. The cells were analyzed 72 hrs post transduction for the expression of the NGFR reporter. (A,B) The effect of the reverse-flow-through method on the % of dendritic cells expressing NGFR. Either retroviral supernatant is applied to the filter before the cells are applied (A) or vice versa (B). (C) Transduction in the absence of the vacuum apparatus with approx. 25% of dendritic cells staining positive.
Figure 8B:
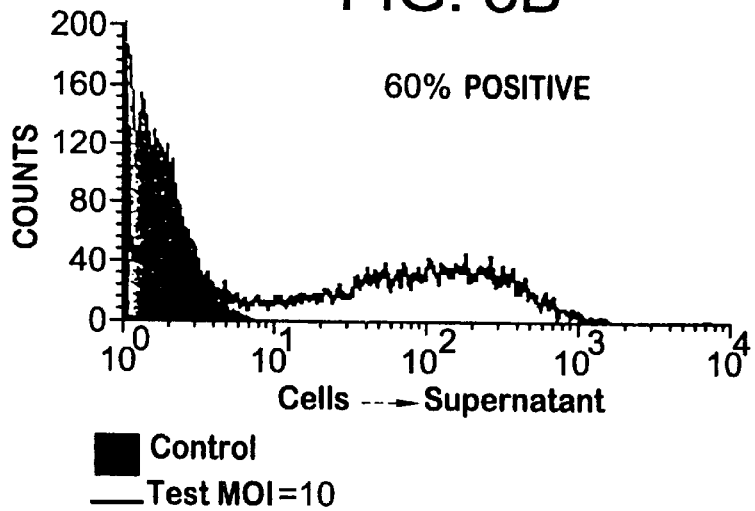
Figure 8C:
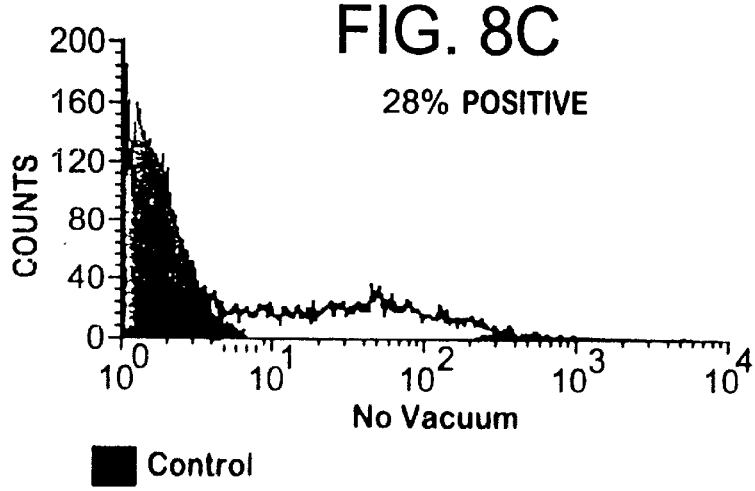

Preliminary experiments with various multiplicities of infection (MOI), presence or absence of GM-CSF and polybrene during transduction demonstrated that retroviruses can transduce less than 30% of dendritic cells (FIG. 8C), which correlates with previously published data. The efficiency of retroviral gene transfer into dendritic cells was enhanced by using a modified version of the vacuum-assisted flow through method as recently published by Chuck and Palsson (supra). By using a MOI of 10 and GM-CSF (800 U/ml) during the procedure, the percentage of transduced cells could be improved from less than 30% to about 60%. The results were the same if either retroviral supernatant was added to the filter followed by addition of the cells (FIG. 8A), or vice versa (FIG. 8B).

In order to show stable integration of HaLMP2a and in the absence of good serological reagents, semi-quantitative PCR was performed at various time points post transduction. Dendritic cells express LMP2A 56 h post transduction using a MOI of 10. These cells were subsequently used to stimulate a CTL response.

Peripheral blood lymphocytes proliferate in response to LMP-2A expressing dendritic cells. To determine whether dendritic cells transduced with the HaLMP-2A retrovirus could stimulate the proliferation of peripheral blood lymphocytes, a tritiated thymidine incorporation assay was performed. Normal donor peripheral blood mononuclear cells were cultured with irradiated dendritic cells that had been transduced with the HaLMP2A retrovirus or a mock plasmid. On days 3, 5, and 10, the cultures were pulsed with (H) thymidine for 6 h and analyzed for radiolabel incorporation. As shown in FIG. 9, mock transduced dendritic cells caused little or no proliferation of the MNCs at all time points at a ratio of 2:1. In contrast, LMP2-transduced dendritic cells induced (H) thymidine incorporation at all time points, at a ration of 2:1, to the same degree as does the donor LCL. Immunophenotyping of the proliferating cells demonstrated both CD8 and CD4 T cells in a ratio of 4:1.

Figure 10A:
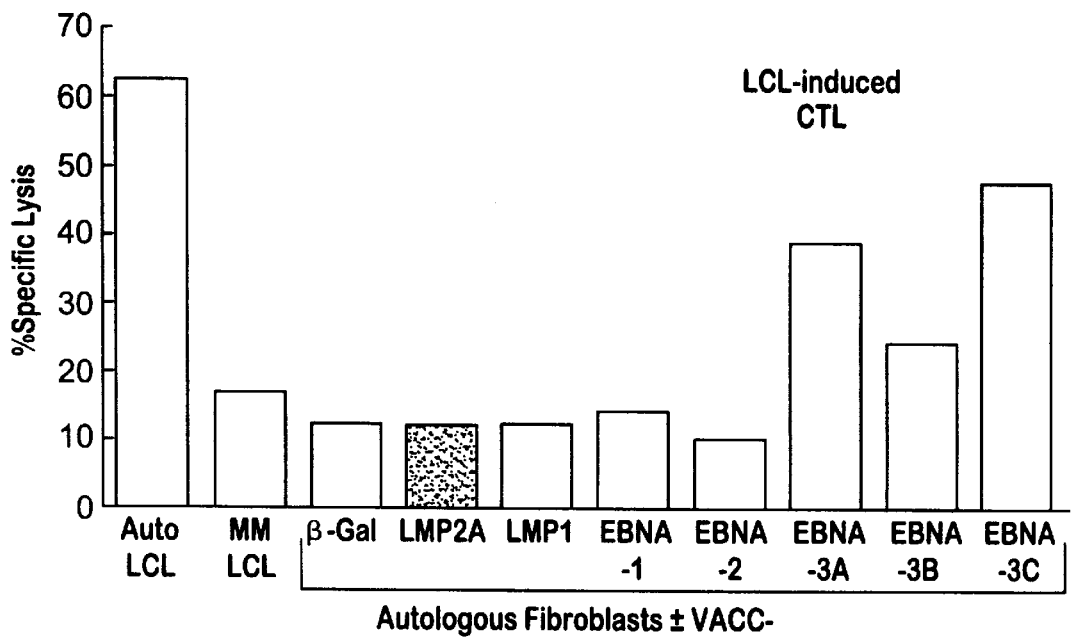
FIGS. 10A–10B. (A) A cytotoxicity profile of a CTL, from a EBV-seropositive donor, induced by a lymphoblastoid cell line. The target cells are autologous fibroblasts infected with vaccinia-EBV constructs, autologous HCL-mismatched LCLS. (B) A cytotoxicity profile of a CTL, from the same EBV-seropositive donor, which has been induced by LMP2A-expressing dendritic cells.
Figure 10B:
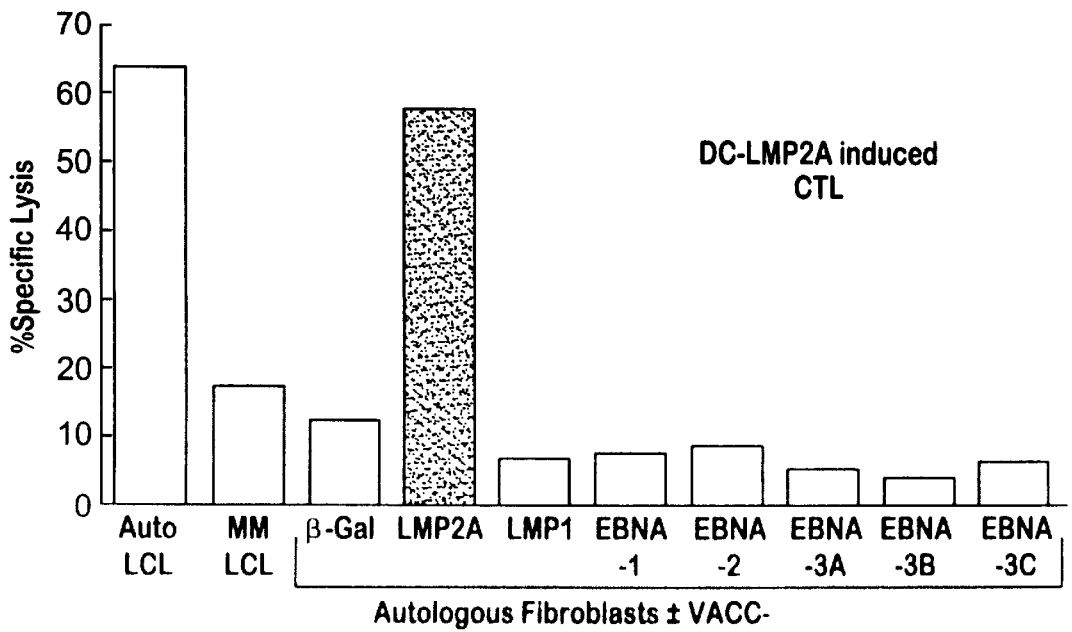

LMP-2A transduced dendritic cells induce LMP-2A specific CTLs from EBV-seropositive donors. Dendritic cells are known to be able to stimulate either a primary or a memory immune response. To test whether HaLMP2A transduced dendritic cells were capable of stimulating a memory immune response, the cytotoxic profile of a CTL induced by a lymphoblastoid cell line was compared to that of a CTL generated by LMP2A-expressing dendritic cells. Donors who were EBV-seropositive and who would, therefore, possess immunological memory to all of the EBV latency proteins were used. The donor's HLA type determines which EBV latency proteins are recognized by the LCL-induced CTL. FIG. 10A shows that this EBV-seropositive donor of HLA type A1, B8,57 DR7, 17 DR52, 53 recognizes EBNA3A, 3B and 3C predominantly with no significant lysis of the LMP2A-expressing target cells. In contrast, FIG. 10B shows the cytotoxic profile of a CTL generated from LMP2A-transduced dendritic cells. This CTL line specific recognizes the LMP2A-expressing fibroblasts and there is now no significant killing of those targets which were recognized by the LCL-induced CTL namely EBNA3A, 3B, or 3C. This illustrates that LMP2A-transduced dendritic cells are capable of stimulating a memory T cell response against an otherwise subdominant antigen.

In the dendritic cell induced CTL lines, the killing of the autologous targets was consistently higher than killing of the HLA mismatched targets over the entire range of effector-to-target ratios. To test whether this lysis was mediated by either CD8$^+$ or CD4$^+$ T cells, blocking antibodies against monomorphic determinants of either HLA-ABC or HLA-DR were added into the assay at an E:T ratio of 40:1. Both antibodies inhibited the CTL-mediated response although the class I antibody effect was the most striking implying that the predominant population of activated T cell were of the CD8$^+$ phenotype.

Figure 11A:
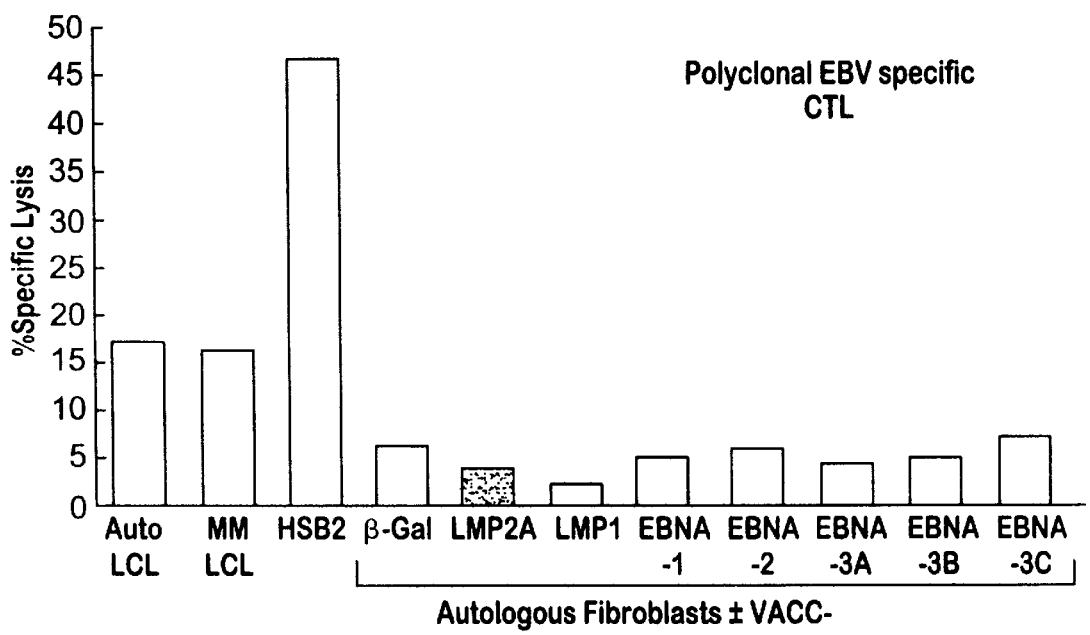
FIG. 11(A, B). Cytotoxicity profiles, as in FIG. 5 above, from EBV-seronegative donors.

LMP-2A transduced dendritic cells can induce LMP2a-specific CTLs from seronegative donors. In order to establish if LMP2A-transduced dendritic cells are capable of inducing a primary response CTL lines from EBV-seronegative donors were generated. FIG. 11A shows the cytotoxic profile of a CTL line induced by the autologous EBV-transformed B cell line from a donor who was HLA A2.1 negative and had no detectable IgG antibodies to EBNA, VCA or EA. As expected, the responding cells proliferated poorly and did not recognize any of the autologous fibroblasts expressing the latency proteins. There was minimal killing of both the autologous and the mismatched LCLS but significant killing of the LAK-sensitive T cell line, HSB2. Phenotyping of the line confirmed that a significant % of CD56 expressing lymphocytes had been induced.

Figure 11B:
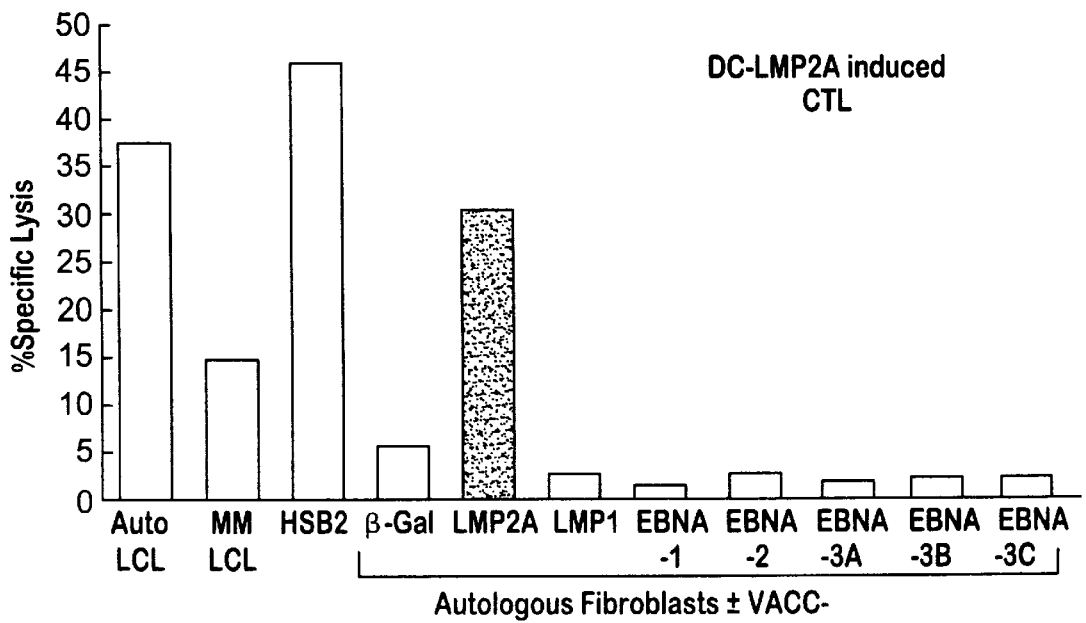

When the autologous LMP2A-transduced dendritic cells were used to initiate a CTL response, the cytotoxicity assay confirmed that this line recognized LMP2A-expressing fibroblasts only (FIG. 11B). Hence, the instant Example shows that by using this system, it is possible to generate an in vitro response in a naive host.

Discussion

EBV-positive Hodgkin tumors only express the weakly immunogenic EBV latency proteins, EBNA1, LMP1, and probably LMP2a. As the cytotoxic precursors to these latent proteins are scanty or absent, this tumor can persist in a host with relatively normal immune function. One possible strategy to overcome the poor immunogenicity of the Hodgkin tumor antigens is to generate tumor-specific CTLs and adoptively transfer them. Such an immunotherapeutic approach would be of benefit to the 10–15% of patients with EBV-positive Hodgkin disease who relapse after therapy. The long term prognosis for this group of patients is grim. In addition, the rate of therapy-related secondary malignancies in Hodgkin survivors is unacceptably high.

The instant Example shows that it is possible to generate LMP2a-specific CTLs using autologous dendritic cells to present the foreign antigen to T cells. Dendritic cells are notoriously difficult to transduce with foreign DNA, however the methods of the present Example utilize a vacuum-assisted retroviral flow-through method whereby dendritic cells are transduced with high efficiency. This method is a modification of that published by Chuck and Palsson (supra) and unexpectedly increases the level of expression from 20–25% without the vacuum, to 55–60% with the vacuum. Although the precise mechanism of this enhanced transduction is not known, it may be partially due to the increased retrovirus to dendritic cell binding ratio, which hence promotes retroviral uptake and subsequent integration. The highly efficiently transduced dendritic cells that present LMP2a stimulate LMP2a-specific CTLs from EBV-seropositive donors who were unable to reactivate LMP2a-specific clones with an autologous lymphoblastoid cell line.

The transduced dendritic cells stimulate a primary immune response to LMP2a. CTL lines from EBV-seronegative donors were generated using the LMP2a-expressing dendritic cells. The lines generated showed highly specific lysis of LMP2a-expressing MHC matched targets. Hence not only can this approach be used to generate responses against weakly immunogenic tumor-associated antigens, it can also do so in unprimed individuals. This activity has not been achieved previously by transducing dendritic cells.

The transduced dendritic cells used to generate the LMP2A-specific CTL lines were not from a pure population, but as seen in the cytotoxicity profile this does not seem to negatively affect the final specificity of the line. Many of patients with relapsed Hodgkin disease have poor peripheral blood counts secondary to salvage treatment. This makes it difficult to obtain enough mononuclear cells to subsequently generate a pure population of dendritic cells and hence therefore an unsorted population was preferably used. The dendritic cells were grown from peripheral blood using GM-CSF and IL-4 as described by Romani et al. Although this method promotes the formation of dendritic cells, a pure population is not obtained and one finds B cells and macrophages in the culture. The macrophage population is kept to a minimum with the addition of IL-4. Moreover, as macrophages also have antigen presenting capabilities, it was not necessary to rigorously deplete the cultures. Although there were B lymphocytes also present, LCLS derived from the EBV-seropositive donors did not induce the formation of LMP2a-specific clones, and therefore it was concluded that these cells do not affect the overall specificity of the final CTL line.

Initial experiments showing transduction of the cells were done on a FACS sorted CD1a pure population, yielding similar results. Accordingly, one may conclude that the method of transduction used in this Example is suitable for transducing dendritic cells with high efficiency to be effective for primary and secondary immune stimulation.

Since retroviruses have been shown to be capable of transducing the dendritic cells, a Harvey murine retroviral backbone was used to clone an LMP2a-containing retroviral construct. The rationale for using LMP2a as opposed to LMP1 is that the latter is known to have oncogenic and immunomodulatory properties. LMP1 was identified as a viral oncogene because of its capacity to transform rat fibroblasts and to render them tumorigenic in nude mice. It also transforms human keratinocytes, inhibits human epithelial cell differentiation, and is cytotoxic when expressed at high levels. LMP2a has not been shown to exhibit any of these characteristics and thus it appears to be more beneficial than LMP1. LMP2a can be detected by RT-PCR of Reed-Sternberg cells, although it is difficult to detect it on the surface of these cells because there are no good serological agents available for either immunofluorescence or Western blotting. Therefore, it is very likely that LMP2a is expressed on the surface of Reed-Sternberg cells.

Recently, replication-defective adenoviruses, containing EBNA3C (RAd-E3C). have been used to reactivate components of EBV-specific CTL memory [Morgan et al, *J. Virol* 70:2394 (1996)]. Good in vitro responses to the antigen, EBNA3C, without ever detecting class I restricted CTL reactivity against the adenoviral proteins. Using donors whose polyclonal CTL response to LCL stimulation contained a strong EBNA3C-specific component, they showed that it was possible to reactivate these CTLs by in vitro stimulation with either RAd-E3C-infected fibroblasts or infected PBMCs. Furthermore, donors whose response to LCL stimulation contained minor EBNA3C reactivity, showed selectively reactivated EBNA3C-specific CTL clones as a result of in vitro stimulation with RAd-E3C-infected PBMCs. Epitope specificity of the responses was also identified at the peptide level. They concluded that their RAd-based system could be applied to screen CTL responses against any tumor-specific target antigen.

The dendritic cell/CTL system described in the instant Example has the advantage of feasibly reactivating specific CTLs against minor components of EBV-specific memory as well as stimulating primary CTL responses. This was done by generating LMP2A-specific CTLs from EBV-seronegative donors who, as expected, were confirmed not to recognize any EBV-infected targets when LCL was used as the stimulator. If LMP2A-expressing dendritic cells from these donors were used to generate CTLs, then a CTL response which was specifically directed against LMP2A-expressing targets was generated. Accordingly, these donors had no immunological memory to EBV and hence this response could not be due to reactivation of EBV-specific memory.

EXAMPLE 3
CTL Response in Vitro Against Adenovirus and FBV

Immunocompromised individuals suffer morbidity and mortality as a result of infection by pathogens that are relatively benign in those with normal immunity. Two such pathogens are EBV and adenoviruses. Recipients of T cell-depleted allogeneic bone marrow are at particularly high risk for these pathogens. Since 1993, these high risk recipients have been treated with donor-derived, EBV-specific CTL as prophylaxis and treatment for EBV-associated lyphoproliferative diseases. This has been highly successful;the procedure is safe, the infused CTL persist long term and provide the recipient with EBV-specific immune responses that can prevent or cure EBV-LPD. This Example describes how adenovirus-pulsed EBV-transformed lymphoblastoid cell lines can be used to generate protective effector lymphocytes against both EBV and adenovirus.

Material and Methods

To generate adenovirus-pulsed LCLS, LCLS were resuspended in serum-free RPMI-1640 at $1\times10^7$ per milliliter and incubated at 37 degrees celsuis for one hour with cesium chloride-gradient purified virions at a multiplicity of 100. Afterwards, the pulsed LCLS were irradiated with 30 Gy and immediately cultured in 24-well plates in complete medium (RPMI supplemented with glutamine, antibiotics and 10% fetal calf serum) at $5\times10^4$ per well along with $2\times10^6$ donor peripheral blood lymphocytes (PBLs). After 10 days of coculture, the viable cells were counted, resuspended in 24-well plates at $1\times10^6$ per well and restimulated with $2.5\times10^5$ irradiated, virion-pulsed LCLS per well. After 4 days, the cultures were fed with 20 units per ml of interleukin-2 and then assayed for their cytotoxicity within 3 to 4 days. A 3- to 4- fold expansion of cells relative to input was usually observed.

Results and Discussion

The first challenge was the selection of the adenovirus type. Because wild-type adenovirus carryover from the culture system might endanger the recipient patient, use of a replication defective mutant was preferred. However, it was uncertain whether active infection would be required to produce an effective CTL response. FIG. 12 shows that adenovirus-specific CTLs can be generated using LCLS pulsed either with wildtype adenovirus or with a replication defective mutant (E4-) can be generated.

Figure 13:
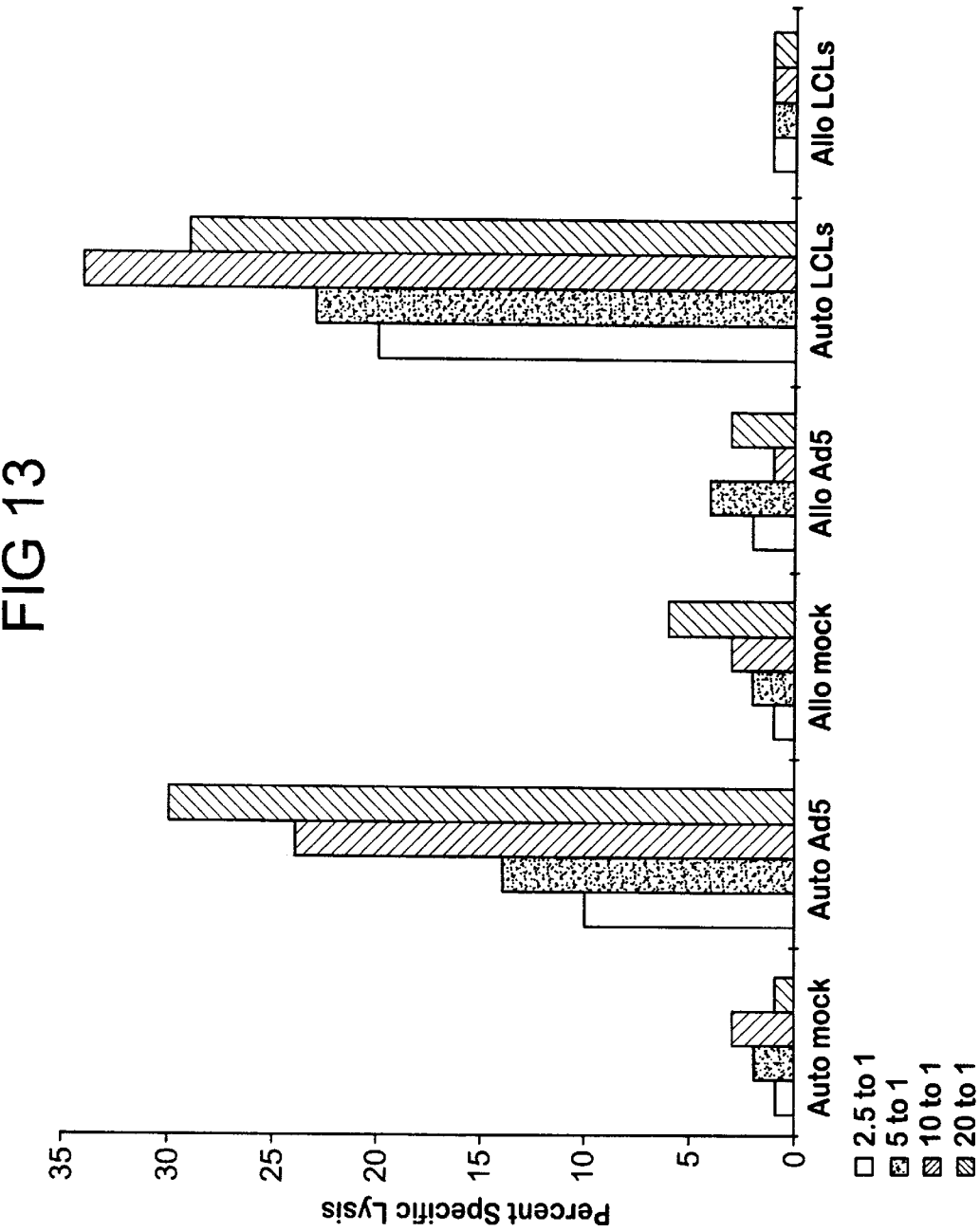
FIG. 13. Adenovirus-pulsed LCLS generate a concomitant response against both adenovirus and EBV. CTLs were prepared as in FIG. 13. In this experiment, LCLS were also included as targets.

To determine whether CTLs generated with autologous adenovirus-pulsed LCLS also contained EBV-specific CTLs, they were tested for their ability to kill both autologous EBV-transformed LCLS and adenovirus-infected fibroblasts. FIG. 13 shows that both adenovirus and EBV infected targets are killed in an HLA-restricted way, showing that both EBV- and adenovirus- specific CTLs were generated.

The greater than 50 serotypes of adenovirus that can be divided into six subgroups. Experiments in the mouse suggested that the CTL response to adenovirus was directed against the E1a proteins and cross-reacted within but not between groups. This was a concern, since members of five of the six groups have reportedly caused disease in BMT recipients. Therefore, experiments were conducted to determine whether CTLs generated against Ad5 would kill cells infected with members of the other groups. We tested the ability of CTLs stimulated with Ad5-pulsed LCLS to kill autologous fibroblasts infected with a representative member of each group. As shown in FIG. 14, fibroblasts infected with all five viruses were killed in an HLA-restricted manner, showing that we will have to stimulate CTLs with only one serotype of adenovirus to protect against all other subtypes. This finding greatly increases the feasibility of the project.

LCLS have long been known to present endogenous EBV proteins or exogenously provided short peptides to T cells. LCL have not been shown to present exogenous proteins and it was unknown whether adenovirus proteins could be presented effectively by LCLS, nor was it known whether simple incubation of virions with LCLS would result in presentation of adenovirus antigens to CTL. In addition, it was not known whether a replication-defective mutant could be used. The present Example establishes that after exposure to exogenously provided adenovirus virions LCLS can present viral antigens via Class I MHC, and that replication incompetent virions suffice for the production of CTLS.

The Example also establishes that adenovirus-pulsed LCLS generate immune responses to both adenovirus and EBV. This obviates the possibility that the immune response to one or the other virus would be immunodominant.

This Example further demonstrates that CTLs with specificity for a range of pathogens can be generated simultaneously using LCLS as antigen-presenting cells. LCLS pulsed with adenovirus and cytomegalovirus (CMV) can be used to generate EBV-, CMV, and adenovirus-specific CTL populations. Additional viral pathogens can be added to this list so that ultimately, BMT recipients can be protected against a wide spectrum of the pathogens which pose problems, using selected T cells that will have no graft versus host activity. Virus-specific CTL (in particular, CMV-specific CTL) will also have wide use in organ transplant recipients and AIDS patients.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

---

What is claimed is:

1. A method for generating viral antigen-specific immune effector cells ex vivo comprising:
   a) pulsing modified antigen presenting cells with viral particles, wherein the antigen presenting cells are modified to process whole viral particles for class I MHC presentation of virus antigens without productive viral infection; and
   b) contacting the pulsed antigen presenting cells with MHC-matched immune effector cells for a time sufficient to stimulate viral antigen-reactive immune effector cells under conditions permissive for proliferation of viral antigen-reactive immune effector cells, whereby viral antigen-specific immune effector cells are induced.

2. The method according to claim 1, further comprising contacting the immune effector cells with additional pulsed modified antigen presenting cells of step (a).

3. The method according to claim 1 wherein the antigen presenting cells are dendritic cells.

4. The method according to claim 3 wherein the dendritic cells are selected from the group consisting of Langerhans cells, follicular dendritic cells, and blood dendritic cells.

5. The method according to claim 1 wherein the antigen presenting cells are lymphoblastoid cell lines.

6. The method according to claim 1 wherein the effector cells comprise cytotoxic T lymphocytes.

7. The method according to claim 1, further comprising pulsing the antigen presenting cells with one or more different viral particles.

8. The method according to claim 1 wherein the virus is selected from the group consisting of adenovirus, cytomegalovirus, Epstein-Barr virus, herpes virus, parainfluenza virus, human immunodeficiency virus (HIV)-1, HIV-2, influenza virus, and rhinovirus.

9. The method according to claim 1 wherein the immune response is a secondary immune response.

10. The method according to claim 3 wherein the immune response is a primary immune response.

11. A method for generating viral antigen-specific immune effector cells or tumor specific antigen-specific immune effector cells ex vivo comprising:
   a. transducing an effective number of antigen presenting cells with a viral vector that expresses a viral antigen or tumor specific antigen under conditions that provide for expression of the antigen; wherein the viral vector is not infective after introduction into the cell; and
   b. contacting the antigen presenting cells with autologous immune effector cells for a time sufficient to stimulate antigen-reactive immune effector cells under conditions permissive for proliferation of antigen-reactive immune effector cells, wherein the viral antigen- or tumor specific antigen-specific immune effector cells are induced that can lyse a MHC-matched target; and wherein said effector cells can be effective:
      (i) for multiple HLA types, and
      (ii) in individuals who have no immunological memory for the tumor specific antigen or the viral antigen.

12. The method according to claim 11 wherein at least 50% of the antigen presenting cells are transduced and express the viral antigen or tumor specific antigen.

13. The method according to claim 11, further comprising contacting the immune effector cells with antigen presenting cells of step (a) more than one time.

14. The method according to claim 11 wherein the antigen presenting cells are dendritic cells.

15. The method according to claim 14 wherein the dendritic cells are selected from the group consisting of Langerhans cells, follicular dendritic cells, and blood dendritic cells.

16. The method according to claim 11 wherein the antigen presenting cells are lymphoblastoid cell line cells.

17. The method according the claim 11 wherein the effector cells include cytotoxic T lymphocytes.

18. The method according to claim 11 wherein the viral antigen is selected from the group consisting of an Epstein-Barr virus antigen, a papillomavirus antigen, a hepatitis A virus antigen, a hepatitis B virus antigen, a hepatitis C virus antigen, a papovavirus antigen, an HIV-1 antigen, an HIV-2 antigen, a human T-lymphotrophic virus (HTLV)-1 antigen, and a HTLV-2 antigen.

19. The method according to claim 11 wherein the tumor antigen is selected from the group consisting of prostate-specific antigen (PSA), human leukemia-associated antigen, carcinoembryonic antigen (CEA), MAGE-1, and MART-1.

20. The method according to claim 11 wherein the immune response is a secondary immune response.

21. The method according to claim 14 wherein the immune response is a primary immune response.

22. Ex vivo antigen presenting cells that present virus antigens for class I MHC from processed whole viral particles, wherein the antigen presenting cells have had whole viral particles introduced into them; wherein said whole viral particles are noninfectious to the antigen presenting cells; and wherein the antigen presenting cells are selected from the group consisting of dendritic cells and lymphoblastoid cells.

23. The antigen presenting cells of claim 22 which are dendritic cells.

24. The antigen presenting cells of claim 22 wherein the dendritic cells are selected from the group consisting of Langerhans cells, follicular dendritic cells, and blood dendritic cells.

25. The antigen presenting cells of claim 22 which are lymphoblastoid cell line cells.

26. The antigen presenting cells of claim 22 wherein the virus antigen is selected from the group consisting of an adenovirus antigen, a cytomegalovirus antigen, an Epstein-Barr virus antigen, a herpes virus antigen, a parainfluenza virus antigen, a human immunodeficiency virus (HIV)-1 antigen, an HIV-2 antigen, an influenza virus antigen, and a rhinovirus antigen.

27. Ex vivo antigen presenting cells transduced with a viral vector that expresses a viral antigen or tumor specific antigen under conditions that provide for expression of the viral antigen or tumor specific antigen; wherein the viral vector is not infective after introduction into the cell; and wherein said antigen presenting cells can be used to generate a population of effector cells that can be effective:

(i) for multiple HLA types, and (ii) in individuals who have no immunological memory for the viral vector, or the tumor specific antigen, or the viral antigen.

28. The antigen presenting cells of claim 27 wherein at least 50% of the antigen presenting cells are transduced and express the viral antigen or tumor specific antigen.

29. The antigen presenting cells of claim 27 which are dendritic cells.

30. The antigen presenting cells of claim 29 wherein the dendritic cells are selected from the group consisting of Langerhans cells, follicular dendritic cells, and blood dendritic cells.

31. The antigen presenting cells of claim 27 which are lymphoblastoid cell line cells.

32. The antigen presenting cells of claim 27 wherein the viral antigen is selected from the group consisting of an Epstein-Barr virus antigen, a papillomavirus antigen, a hepatitis A virus antigen, a hepatitis B virus antigen, a hepatitis C virus antigen, a papovavirus antigen, an HIV-1 antigen, an HIV-2 antigen, a human T-lymphotrophic virus (HTLV)-1 antigen, and a HTLV-2 antigen.

33. The antigen presenting cells of claim 27 wherein the tumor antigen is selected from the group consisting of prostate-specific antigen (PSA), human leukemia-associated antigen, carcinoembryonic antigen (CEA), MAGE-1, and MART-1.

* * * * *